(12) United States Patent
Stone et al.

(10) Patent No.: US 10,070,779 B2
(45) Date of Patent: Sep. 11, 2018

(54) DENTAL LIGHT USING LEDS

(71) Applicant: A-dec, Inc., Newberg, OR (US)

(72) Inventors: Christopher C. Stone, Newberg, OR (US); Takaaki Nakagawa, Camas, WA (US); Eric Bube, West Linn, OR (US); Randall Joel Lonsdale, Beaverton, OR (US); Patrick W. Berry, Vancouver, WA (US); Ryan M. Williams, Newberg, OR (US); Joseph Van Domelen, Hillsboro, OR (US); Jason Alvarez, Portland, OR (US); Jonathan E. Myers, Portland, OR (US)

(73) Assignee: A-dec, Inc., Newberg, OR (US)

( * ) Notice: Subject to any disclaimer, the term of this patent is extended or adjusted under 35 U.S.C. 154(b) by 0 days.

(21) Appl. No.: 15/830,410

(22) Filed: Dec. 4, 2017

(65) Prior Publication Data

US 2018/0184890 A1   Jul. 5, 2018

Related U.S. Application Data

(63) Continuation of application No. 15/290,705, filed on Oct. 11, 2016, now Pat. No. 9,833,133, which is a
(Continued)

(51) Int. Cl.
*F21V 7/00* (2006.01)
*A61B 1/06* (2006.01)
(Continued)

(52) U.S. Cl.
CPC ............. *A61B 1/0684* (2013.01); *A61B 1/24* (2013.01); *A61C 1/088* (2013.01); *F21K 9/62* (2016.08);
(Continued)

(58) Field of Classification Search
CPC . F21V 5/002; F21V 5/007; F21V 5/04; F21V 11/08; F21V 21/26; F21V 21/28;
(Continued)

(56) References Cited

U.S. PATENT DOCUMENTS 1,864,756 A   6/1932  Pieper
2,231,719 A   2/1941  Hughey
(Continued)

FOREIGN PATENT DOCUMENTS

AU         327125      8/2009
CN    101806411 A      8/2010
(Continued)

OTHER PUBLICATIONS

A-dec, Inc., "A-dec 500 Brochure," http://us.a-dec.com/en/Products/Dental-Lights/A-dec-500, downloaded Dec. 16, 2011.
(Continued)

*Primary Examiner* — Bryon T Gyllstrom
(74) *Attorney, Agent, or Firm* — Klarquist Sparkman, LLP

(57) ABSTRACT

A dental light comprises at least one light emitting diode light source configured to produce a light beam and at least one collimating lens system situated to receive the light beam. The collimating lens system is configured to collect and collimate the light beam. The collimating lens system can additionally modify the beam through controlled diffusion or shape the beam using an aperture.

12 Claims, 14 Drawing Sheets

Related U.S. Application Data continuation of application No. 13/281,379, filed on Oct. 25, 2011, now Pat. No. 9,500,340.

(51) Int. Cl.

| | | |
|---|---|---|
| *F21V 33/00* | (2006.01) | |
| *F21V 29/70* | (2015.01) | |
| *F21V 11/08* | (2006.01) | |
| *G02B 27/30* | (2006.01) | |
| *F21V 31/00* | (2006.01) | |
| *F21K 9/62* | (2016.01) | |
| *F21V 21/30* | (2006.01) | |
| *F21V 29/507* | (2015.01) | |
| *F21V 21/28* | (2006.01) | |
| *F21V 5/00* | (2018.01) | |
| *A61C 1/08* | (2006.01) | |
| *F21V 21/26* | (2006.01) | |
| *F21V 23/00* | (2015.01) | |
| *A61B 1/24* | (2006.01) | |
| *F21V 5/04* | (2006.01) | |
| *F21Y 105/10* | (2016.01) | |
| *F21Y 115/10* | (2016.01) | |
| *F21W 131/202* | (2006.01) | |
| *F21Y 101/00* | (2016.01) | |

(52) U.S. Cl.
CPC .............. *F21V 5/002* (2013.01); *F21V 5/007* (2013.01); *F21V 5/04* (2013.01); *F21V 11/08* (2013.01); *F21V 21/26* (2013.01); *F21V 21/28* (2013.01); *F21V 21/30* (2013.01); *F21V 23/005* (2013.01); *F21V 29/507* (2015.01); *F21V 29/70* (2015.01); *F21V 31/005* (2013.01); *F21V 33/0068* (2013.01); *G02B 27/30* (2013.01); *F21W 2131/202* (2013.01); *F21Y 2101/00* (2013.01); *F21Y 2105/10* (2016.08); *F21Y 2115/10* (2016.08)

(58) Field of Classification Search
CPC ...... F21V 21/30; F21V 23/005; F21V 31/005; F21V 33/0068; F21V 29/507; F21V 29/70; G02B 27/30; A61B 1/0684; A61B 1/24; F21K 29/70; F21K 9/62; A61C 1/088
USPC ........................................................ 362/247
See application file for complete search history.

(56) References Cited

U.S. PATENT DOCUMENTS

| | | | |
|---|---|---|---|
| 2,540,577 A | 2/1951 | Greppin | |
| 3,183,773 A | 5/1965 | Weinstein | |
| 4,774,643 A | 9/1988 | McGinnis et al. | |
| 4,777,574 A | 10/1988 | Eisner | |
| 4,829,407 A | 5/1989 | Bushell et al. | |
| 4,837,668 A | 6/1989 | Koehler | |
| 4,930,058 A | 5/1990 | Jones et al. | |
| 4,963,798 A | 10/1990 | McDermott | |
| 4,975,826 A | 12/1990 | Bell | |
| 5,066,889 A | 11/1991 | Edwards | |
| 5,174,649 A | 12/1992 | Alson | |
| 5,268,977 A | 12/1993 | Miller | |
| 5,803,729 A | 9/1998 | Tsimerman | |
| 5,816,681 A * | 10/1998 | Tedesco | F21V 5/002 362/459 |
| 5,908,294 A | 6/1999 | Schick et al. | |
| 5,967,653 A | 10/1999 | Miller | |
| 6,012,827 A | 1/2000 | Caplan et al. | |
| 6,249,375 B1 | 6/2001 | Silhengst et al. | |
| 6,290,368 B1 | 9/2001 | Lehrer | |
| 6,459,919 B1 | 10/2002 | Lys et al. | |
| 6,478,453 B2 | 11/2002 | Lammers et al. | |
| 6,513,962 B1 | 2/2003 | Mayshack et al. | |
| 6,520,666 B1 | 2/2003 | Beyerlein et al. | |
| 6,626,556 B2 | 9/2003 | Galli | |
| 6,692,251 B1 | 2/2004 | Logan et al. | |
| 6,705,745 B1 | 3/2004 | Pederson | |
| 6,827,468 B2 | 12/2004 | Galli | |
| 6,926,524 B2 | 8/2005 | Cao | |
| 6,929,390 B2 | 8/2005 | Amano | |
| 6,942,365 B2 | 9/2005 | Galli | |
| 6,994,451 B2 | 2/2006 | Galli | |
| 7,186,004 B2 * | 3/2007 | Powell | G02B 3/0025 359/365 |
| 7,207,694 B1 | 4/2007 | Petrick | |
| 7,275,931 B2 | 10/2007 | Katsuda et al. | |
| 7,331,681 B2 | 2/2008 | Pohlert et al. | |
| 7,425,077 B2 | 9/2008 | Lockamy et al. | |
| 7,450,028 B2 | 11/2008 | De Godzinsky | |
| D607,142 S | 12/2009 | Alvarez | |
| 7,665,875 B2 | 2/2010 | Whitman | |
| 8,016,470 B2 | 9/2011 | Li et al. | |
| 8,388,205 B2 | 3/2013 | Swayne et al. | |
| 8,459,852 B2 | 6/2013 | Bria et al. | |
| 8,931,942 B2 | 1/2015 | Bria et al. | |
| 2002/0181231 A1 * | 12/2002 | Luk | F21V 5/008 362/240 |
| 2003/0133300 A1 | 7/2003 | Wang et al. | |
| 2003/0223248 A1 | 12/2003 | Cronin et al. | |
| 2004/0130892 A1 | 7/2004 | Galli | |
| 2004/0130894 A1 | 7/2004 | Galli | |
| 2004/0141316 A1 | 7/2004 | Twardawski | |
| 2004/0141336 A1 | 7/2004 | West et al. | |
| 2004/0240201 A1 | 12/2004 | Rausseck | |
| 2005/0036307 A1 | 2/2005 | Wang | |
| 2005/0152146 A1 * | 7/2005 | Owen | A61L 2/10 362/294 |
| 2005/0225959 A1 | 10/2005 | Pohlert et al. | |
| 2006/0002135 A1 | 1/2006 | Kokeny et al. | |
| 2006/0039160 A1 | 2/2006 | Cassarly et al. | |
| 2007/0190479 A1 | 8/2007 | Jackson et al. | |
| 2008/0025013 A1 | 1/2008 | Lockamy et al. | |
| 2008/0130309 A1 | 6/2008 | Condon et al. | |
| 2008/0238323 A1 * | 10/2008 | Chan | F21V 29/004 315/35 |
| 2008/0239697 A1 * | 10/2008 | Katsuda | A61B 1/24 362/33 |
| 2009/0091913 A1 | 4/2009 | Li et al. | |
| 2009/0116214 A1 | 5/2009 | Phillips et al. | |
| 2009/0116225 A1 | 5/2009 | Feinbloom et al. | |
| 2009/0296408 A1 * | 12/2009 | Hendriks | F21V 14/003 362/311.01 |
| 2009/0318771 A1 | 12/2009 | Marka et al. | |
| 2010/0027251 A1 | 2/2010 | Shpizel | |
| 2010/0110686 A1 | 5/2010 | Li et al. | |
| 2010/0188018 A1 * | 7/2010 | Salm | F21V 7/00 315/294 |
| 2010/0203465 A1 | 8/2010 | Bria et al. | |
| 2014/0301071 A1 * | 10/2014 | Jorgensen | F21V 14/06 362/231 |
| 2015/0062957 A1 | 3/2015 | Bria et al. | |
| 2015/0292684 A1 | 10/2015 | Hackel | |

FOREIGN PATENT DOCUMENTS

| | | |
|---|---|---|
| CN | 200930194874.5 | 9/2010 |
| EP | 001153993-0004 | 7/2009 |
| EP | 2204604 A1 | 7/2010 |
| EP | 2587128 A1 | 5/2013 |
| EP | 2469158 | 10/2015 |
| EP | 2469159 | 10/2015 |
| JP | 00/217844 | 8/2000 |
| JP | 1398487 | 9/2010 |
| KR | 0582230 | 12/2010 |
| WO | WO 01/57431 | 8/2001 |
| WO | WO 01/75487 | 10/2001 |
| WO | WO 02/06723 | 1/2002 |
| WO | WO 02/06798 | 1/2002 |
| WO | WO 02/80808 | 10/2002 |

(56) References Cited

FOREIGN PATENT DOCUMENTS

| WO | WO 03/60495 | 7/2003 |
|---|---|---|
| WO | WO 05/06818 | 1/2005 |
| WO | WO 2009/045223 | 4/2009 |
| WO | WO 2009/045251 | 4/2009 |
| WO | WO 2011/094249 | 8/2011 |

OTHER PUBLICATIONS

A-dec, Inc., "A-dec 300 Brochure," http://us.a-dec.com/en/Products/Dental-Lights/A-dec-300, downloaded Dec. 16, 2011.
A-dec, Inc., "A-dec 6300 Dental Light Brochure," http://us.a-dec.com/en/Products/Dental-Lights/6300, downloaded Dec. 16, 2011.
A-dec, Inc., "Performer Brochure," http://us.a-dec.com/en/Products/Dental-Lights/Performer, downloaded Dec. 16, 2011.
Belmont Equipment, "Product Overview: Bel-Halo Bel-Halo Lights," http://dental.takarabelmont.com/lights/Bel-Halo-Lights, downloaded Aug. 22, 2011.
Belmont Equipment, "Product Brochure: Bel-Halo LED Dental Lights," http://dental.takarabelmont.com/lights/Bel-Halo-Lights, downloaded Aug. 22, 2011.
DentalEzGroup, "Everlight," http://www.dentalez.com/dentalez/dental-operatory-lights/everlight.html, downloaded Aug. 22, 2011.
DentalEzGroup, "Everlight eBrochure," http://www.dentalez.com/dentalez/dental-operatory-lights/everlight.html, downloaded Dec. 18, 2011.
European Extended Search Report for European Patent Application No. 16195863.2, dated Mar. 28, 2017.
Forest Dental Products Inc., "Forest 2011 Equipment Catalogs," pp. 74-76, http://www.forestmed.com, downloaded Dec. 18, 2011.
Faro S.p.A., "Alya LED Dental Operating Light," http://www.faro.it/en/alya-led-dental-operating-light, downloaded Dec. 14, 2011.
Planmeca U.S.A. Inc, "SingLED Operatory Light," http://www.planmecausa.com/singled-operatory-light-products-2.php-?page_id=4, downloaded Dec. 14, 2011.
Planmeca U.S.A. Inc, "SingLED Operatory Light Brochure," http://www.planmecausa.com/singled-operatory-light-products-2.php-?page_id=4, downloaded Dec. 14, 2011.
Pelton & Crane "Helios 3000 Brochure" http://www.pelton.net/customer-center/brochures/, downloaded Dec. 18, 2011.
degré K, "LOLé$^2$," http://www.degrek.com/en/products/lole/, downloaded Dec. 18, 2011.
Schreiber et al., "Homogenous LED-Illumination Using Microlens Arrays," Proceedings SPIE 5942, 59420K (2005).
Communication pursuant to Article 94(3) EPC from the European Patent Office, dated Nov. 28, 2013, regarding European Patent Application No. 12184900.4, 4 pages.
Communication pursuant to Article 94(3) EPC from the European Patent Office, dated Jul. 21, 2014, regarding European Patent Application No. 12184900.4, 5 pages.
Office Action from the United States Patent & Trademark Office in co-pending U.S. Appl. No. 13/281,379, dated Jan. 29, 2015.
Office Action from the United States Patent & Trademark Office in co-pending U.S. Appl. No. 13/281,379, dated Aug. 25, 2015.
Office Action and Search Report from the State Intellectual Property Office of the People's Republic of China (with English Translation), for Chinese Patent Application No. 201210412974.1, dated Jan. 27, 2016, 15 pages.
Office Action from the United States Patent & Trademark Office in co-pending U.S. Appl. No. 13/281,379, dated Feb. 2, 2016.
"Communication—European Search Report" from the European Patent Office for European Application No. EP12 184 900.4-1757, dated Feb. 11, 2016, 4 pages.
Notice of Allowance from the United States Patent & Trademark Office in co-pending U.S. Appl. No. 13/281,379, dated May 19, 2016.
Notice of Allowance from the United States Patent & Trademark Office in co-pending U.S. Appl. No. 13/281,379, dated Jul. 11, 2016.

* cited by examiner

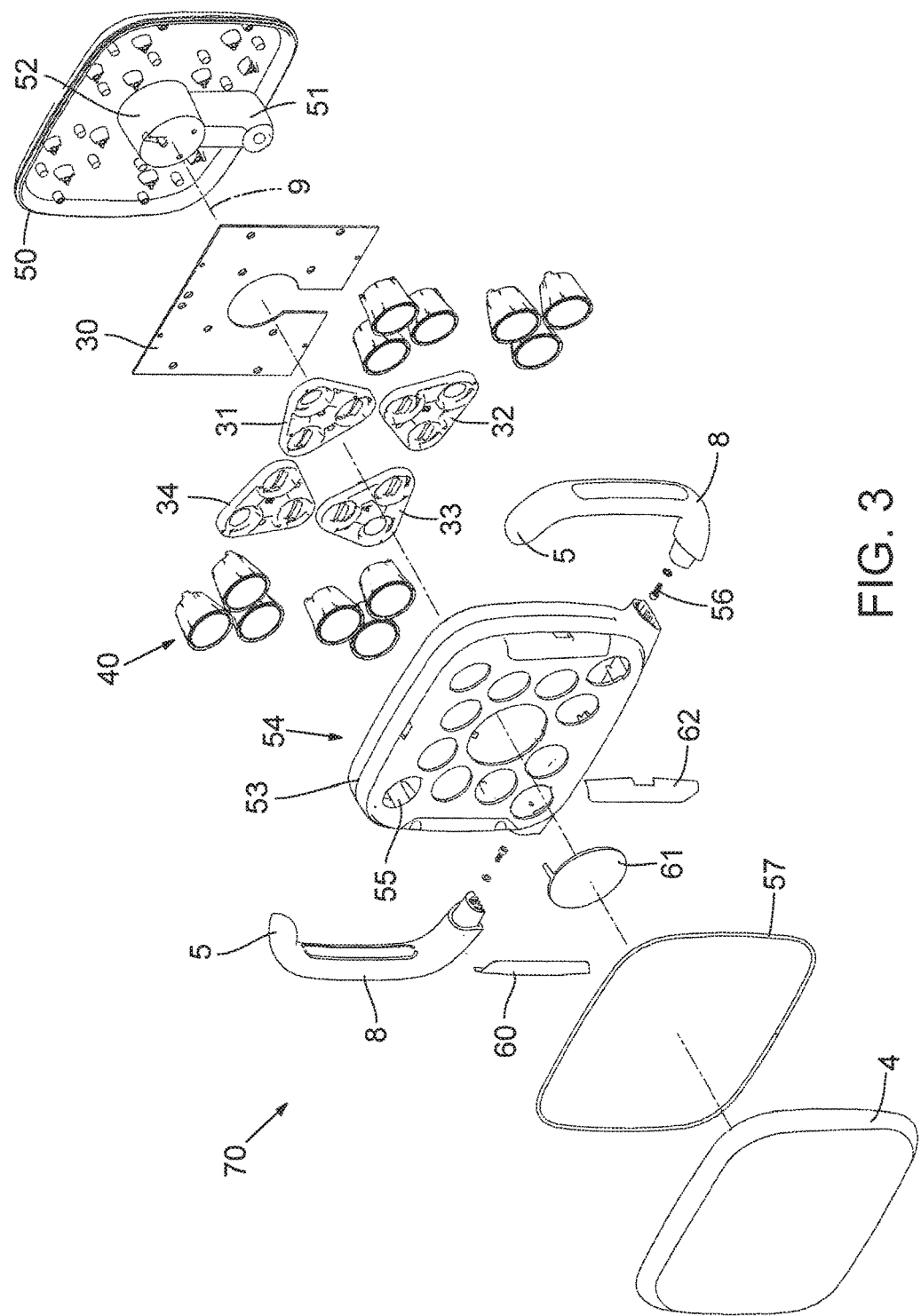

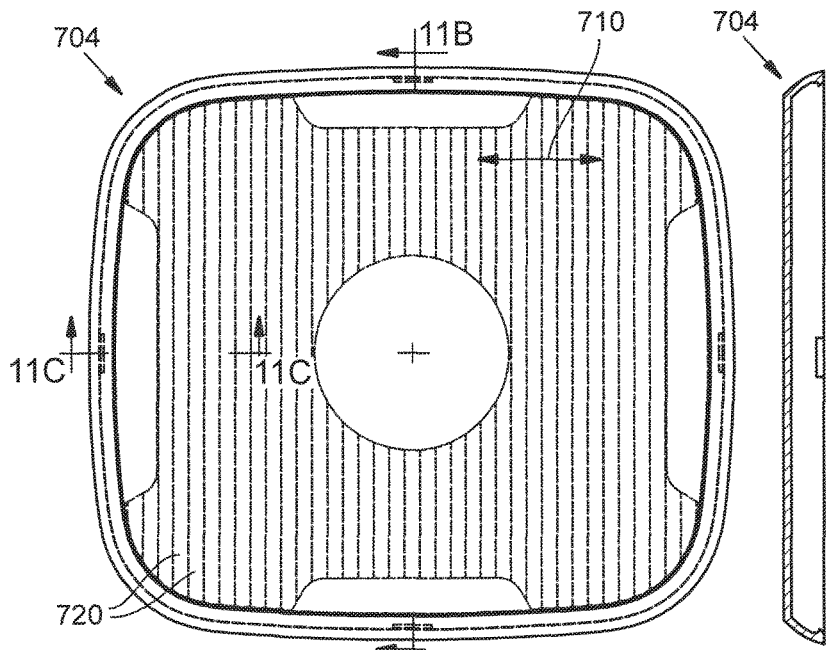
FIG. 11A
FIG. 11B
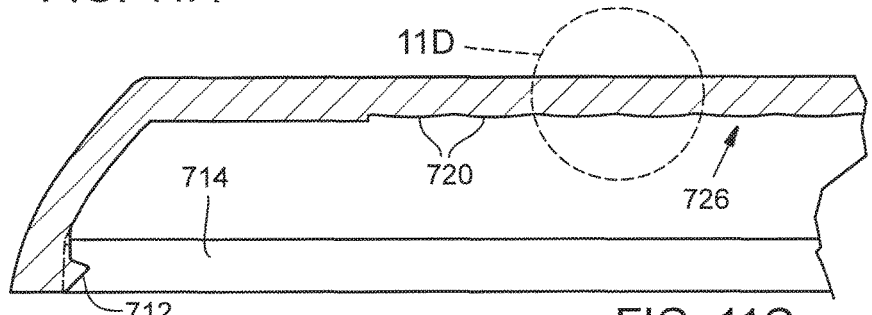
FIG. 11C
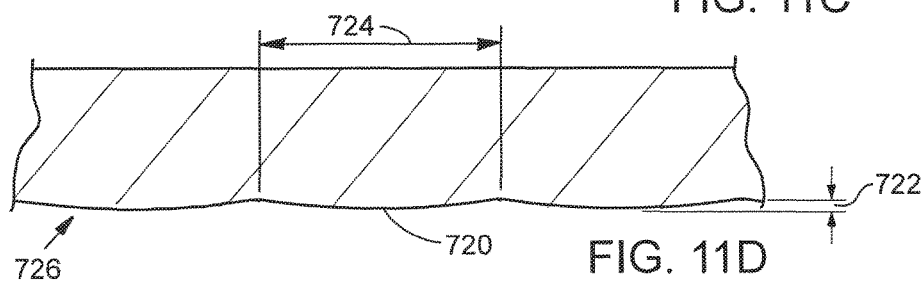
FIG. 11D

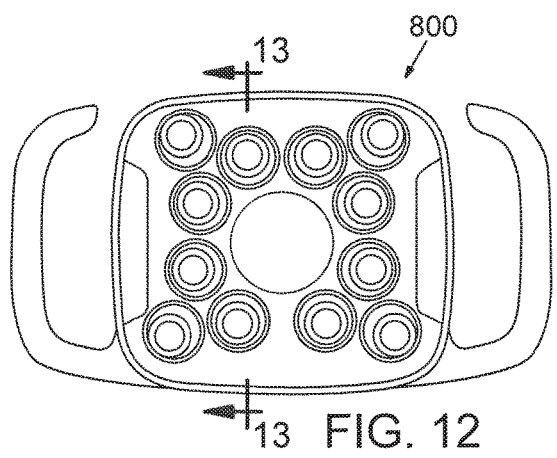
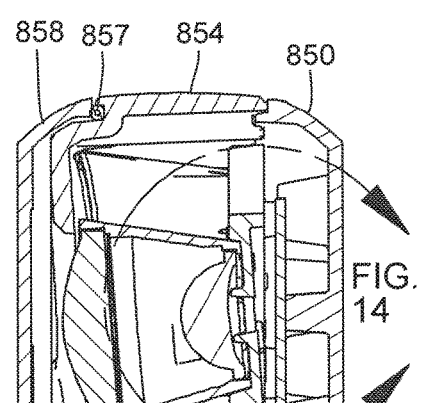
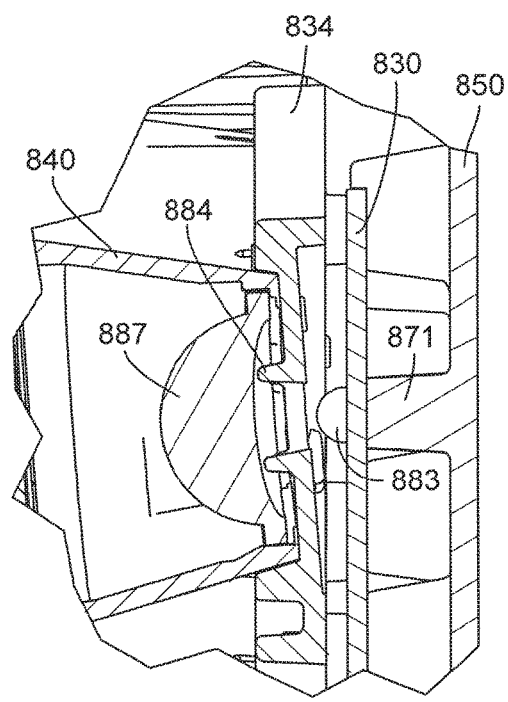
FIG. 12
FIG. 14
FIG. 13

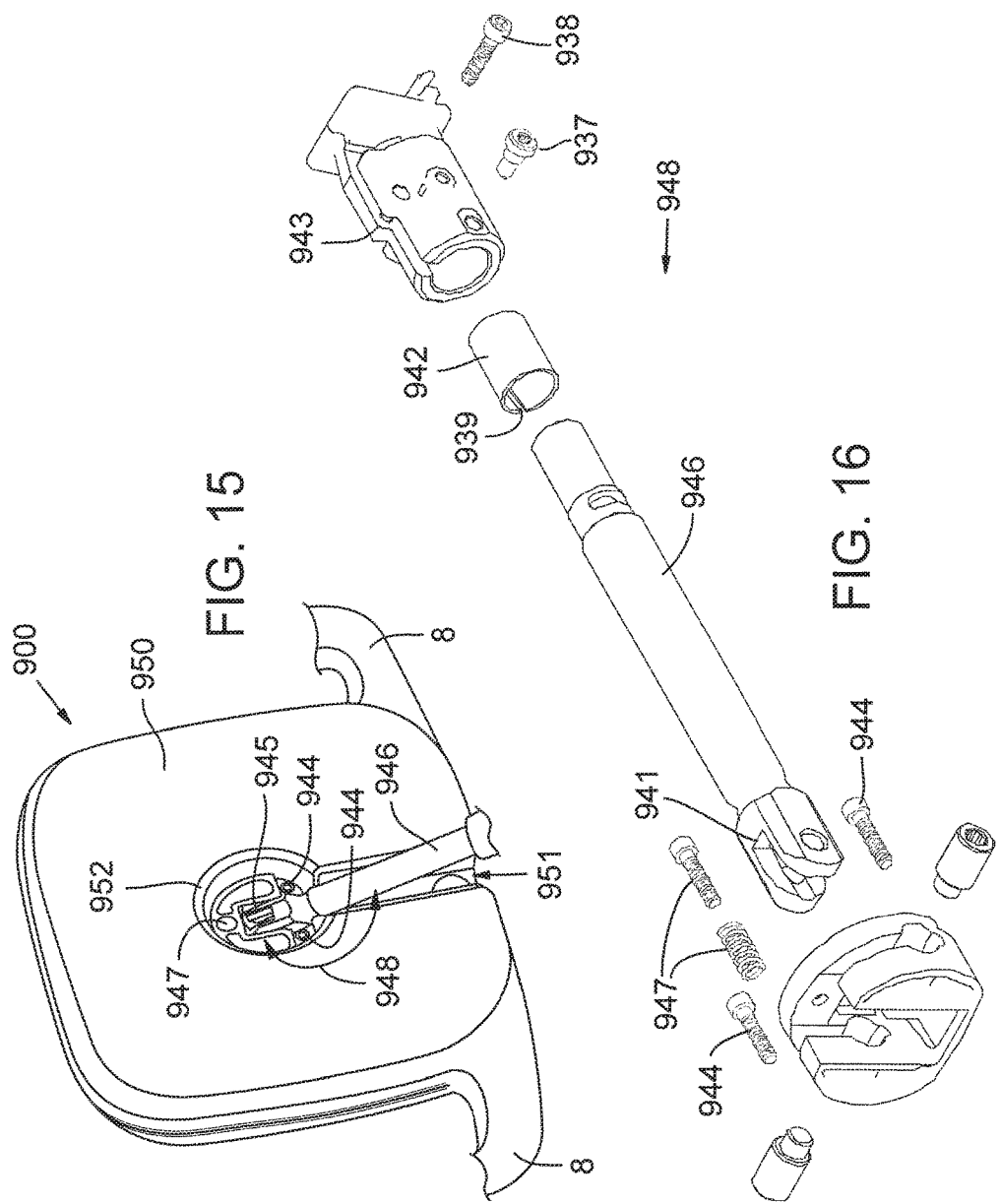

DENTAL LIGHT USING LEDS

CROSS-REFERENCE TO RELATED APPLICATION

This present application is a continuation of U.S. patent application Ser. No. 15/290,705, filed Oct. 16, 2016, which claims the benefit of U.S. patent application Ser. No. 13/281,379, filed Oct. 25, 2011, which are incorporated herein by reference.

FIELD

This application relates to LED lights, and, in particular, an LED light for use in dentistry.

BACKGROUND

In the dental industry, dental lights, also known as dental operating lights or dental operating luminaries, are used to illuminate a patient's mouth (oral cavity) while dental procedures are performed. For example, dental lights assist in the examination and diagnosis of patients, tooth reduction and preparation, color-shade matching, and restoration.

Current dental lights use predominantly incandescent or quartz-halogen bulbs as the light source. These sources are also commonly used with reflectors, such as mirrors or other reflective surfaces. Light emitting diode (LED) light sources have several advantages over these light sources, including longer life, lower power consumption, and greatly reduced radiant heat.

There are, however, several challenges to implementing LED light sources in dental lights. For example, quality of light is important in various dental applications. The color rendering index (CRI) of an LED is typically lower than that of conventional light sources, making it difficult for dentists to examine for soft tissue pathology and to perform color-shade matching with LED light.

Another design concern is that the dental light should create a light pattern that reduces operator and patient discomfort. For example, it is desirable to reduce operator eye fatigue, to reduce shadowing, and to reduce light incident on the patient's eyes. Thus, there are several important considerations to take into account in the design of an LED dental light.

SUMMARY

Described below are embodiments of a dental light having LED light source(s) that addresses some of the shortcomings of conventional dental lights.

According to one embodiment, a dental light comprises at least one light emitting diode (LED) light source configured to produce a light beam along a path, and at least one collimating lens system situated to receive the light beam and configured to mix light within the light beam by controlled diffusion to increase color uniformity of the light beam. The at least one collimating lens system can comprise a diffuser configured to produce the controlled diffusion. The diffuser can be a transparent optical element having a microstructured surface. The diffuser can be configured to impose a divergence on the received light beam of between about 0.5 and about 5 degrees, or of about 2 degrees. The at least one collimating lens system can comprise a first lens, a second lens, and a diffuser positioned between the first and the second lens. The first lens can be an aspheric collector lens and the second lens can be a plano-convex collimator lens situated downstream of the first lens. The at least one collimating lens system can comprise an aperture and a diffuser, where the diffuser is configured to produce the controlled diffusion and is situated downstream from the aperture. The LED light source can be a high brightness white LED.

According to another embodiment, a dental light comprises a plurality of LED light sources configured to produce respective light beams along respective paths and a plurality of collimating lens systems each situated to receive the light beams and configured to mix light within the light beams by controlled diffusion to produce respective diffused light beams. The plurality of collimating lens systems can be spaced apart from each other and situated so as to direct the respective diffused light beams towards a projection axis of the dental light. The plurality of collimating lens systems can be arranged approximately equidistant from a central point so as to define a polygon-shaped array, or to define a substantially circular array. The central point can be along the projection axis of the dental light. The plurality of collimating lens systems can be situated relative to each other such that the diffused light beams substantially overlap at a predetermined illumination plane of the dental light. The diffused light beams can produce respective beam patterns at the illumination plane, and the dental light can include at least one shaping lens configured to receive the diffused light beams and to spread the respective beam patterns in the illumination plane. The plurality of collimating lens systems can be situated relative to each other so as to reduce hard shadows of the diffused light beams at the illumination plane. The plurality of collimating lens systems can be situated relative to each other so as to reduce change in beam pattern size as distance from the illumination plane varies. The illumination plane can be substantially perpendicular to the projection axis of the dental light. The illumination plane can be located between about 550 and 850 millimeters, or between about 700 and 750 millimeters, from the LED light sources along the projection axis.

In another embodiment, a dental light comprises at least one normal-mode illuminator and at least one cure-safe illuminator. The at least one normal-mode illuminator can be formed from at least one LED light source and at least one collimating lens system. The at least one cure-safe illuminator can be formed from at least one LED light source and at least one collimating lens system configured to produce a cure-safe beam. The at least one cure-safe illuminator can comprise a band pass filter configured to produce the cure-safe beam. Collimating lens systems can be configured to mix light within the light beams produced by the LED light sources by controlled diffusion to increase color uniformity of the light beams.

According to another embodiment, a dental light comprises at least one light emitting diode (LED) light source mounted to a substrate and at least one collimating lens system. The at least one LED light source is configured to produce a light beam along a normal axis that is perpendicular to the substrate at an approximate center of the at least one LED light source. The light beam contains light having a plurality of angles of propagation relative to the normal axis. The at least one LED light source has a color rendering index (CRI). In one implementation, the at least one collimating lens system is situated to receive the light beam and configured to limit the angles of propagation of light collected by the collimating lens system such that the light emitted from the at least one collimating lens system has a CRI that is at least about 2 points greater than the CRI of the at least one LED light source. In another implementation, the at least one collimating lens system is situated to receive the light beam and configured to limit the angles of propagation of light collected by the collimating lens system so as to produce a shift in CIE chromaticity coordinates of the LED light source towards a Planckian black body locus of at least 0.002 units, or of at least 0.004 units. The shift can be such that CIE x and y chromaticity coordinates of the LED light source after being shifted lie approximately on the Planckian black body locus. The at least one collimating lens system can be configured to predominantly collect light emitted from the LED light source having angles of propagation less than about 60 degrees. The at least one collimating lens system can comprise an aperture configured to limit the angles of propagation of light collected by the collimating lens system.

According to another embodiment, a dental light comprises a plurality of light emitting diode (LED) light sources spaced apart and mounted on a substrate, each configured to produce respective light beams. The dental light also comprises corresponding plurality of transmissive optical systems situated so as to receive the respective light beams and configured to collimate the light beams, thereby producing respective collimated light beams such that each collimated light beam produces a beam pattern at a predetermined illumination plane spaced from the substrate along an illumination axis of the respective transmissive optical system. The dental light also comprises a transparent shield positioned to receive the collimated light beams and configured to refract the collimated light beams along a refraction axis so as to spread the respective beam patterns along the refraction axis. The refraction axis can be parallel to the shield. The shield can comprise a series of lenses which extend along an inner surface of the shield in a direction perpendicular to the refraction axis, each of the lenses having a width along the refraction axis such that each collimated light beam is transmitted through more than one of the lenses. The shield can comprise an array of cylindrical convex lenses perpendicular to the refraction axis to perform the refraction of the light beams. The cylindrical convex lenses can be formed on an inner surface of the shield. The plurality of transmissive optical systems can be positioned such that the respective illumination axes form an angle of between about 1 and about 10 degrees with a projection axis of the dental light. The illumination plane can be located at a distance of between about 550 and about 800 mm from the substrate. The dental light can further comprise a rear housing and a front housing intermediate the shield and the rear housing. The substrate can be mounted to an inside surface of the rear housing. The shield, the front housing and the rear housing can be configured to be assembled together into an enclosed optical system.

According to another embodiment, the dental light comprises a housing formed of a thermally conductive material, a thermally conductive printed circuit board shaped to fit within the housing and positioned in direct thermal contact with the housing, and a plurality of light emitting diode (LED) light sources coupled to the circuit board. The direct thermal contact between the printed circuit board and the housing facilitates dissipation of heat generated by the LED light sources. The thermally conductive printed circuit board can comprise a circuit layer, a dielectric layer comprising a dielectric material, and a thermally conductive substrate layer comprising aluminum or copper. The dielectric layer can have a thickness of about 0.003" or less and the circuit layer can have a thickness of about 2 ounces/square feet or greater. The plurality of LED light sources can be spatially separated on the thermally conductive printed circuit board by a distance of about 1.4" or greater.

According to another embodiment, a dental light comprises at least one light emitting diode (LED) light source mounted to a substrate and at least one collimating lens system comprising an aperture. The least one LED light source is configured to produce a light beam along a normal axis that is perpendicular to the substrate at an approximate center of the at least one LED light source. The light beam contains light having a plurality of angles of propagation relative to the normal axis and the plurality of angles represents an angular distribution of the light beam. The aperture is situated to receive the light beam and configured to shape the light beam such that the angular distribution is reduced along a first axis perpendicular to the normal axis, thereby producing a shaped light beam. The reduced angular distribution along the first axis corresponds with a reduction in patient eye glare at a predetermined illumination plane. The aperture can have a substantially rectangular shape. The at least one collimating lens system can comprise collimating optics, and the aperture can be positioned between the LED light source and the collimating optics. The aperture can have a short axis that corresponds to the first axis.

In one example, the dental light further comprises at least one shaping lens situated downstream from the collimating optics, where the at least one shaping lens being is configured to receive the shaped light beam and to spread the light beam in the illumination plane to further reduce patient eye glare. In another example, the collimating lens system comprises a diffuser configured to mix light within the light beam by controlled diffusion to increase color uniformity of the light beam. The collimating lens system can comprise a collector lens situated upstream from the diffuser and downstream from the aperture. In another example, the at least one collimating lens system comprises a total internal reflection (TIR) collimator configured to mix light within the light beam to increase color uniformity of the light beam. The at least one collimating lens system can comprise a first lens and a total internal reflection (TIR) collimator situated upstream of the first lens. In another example, the dental light further comprises a transparent shield positioned downstream from the collimating lens system and comprising an array of cylindrical convex lenses.

According to another embodiment, the dental light comprises a plurality of LED light sources spaced apart and mounted to the substrate and a plurality of collimating lens systems comprising respective apertures. Each LED light source is configured to produce respective light beams along respective normal axes, and each collimating lens system is situated to receive the light beams. The apertures are configured to produce respective shaped light beams. The plurality of collimating lens systems are situated so as to direct the respective shaped light beams towards a projection axis of the dental light.

According to another embodiment, a dental light comprises at least one normal-mode illuminator and at least one cure-safe illuminator. The at least one normal-mode illuminator can be formed from at least one LED light source and at least one collimating lens system. The at least one cure-safe illuminator can be formed from at least one LED light source and at least one collimating lens system configured to produce a cure-safe beam. Collimating lens systems can comprise apertures configured to produce respective shaped light beams. The at least one normal-mode illuminator is configured and situated to produce respective normal-mode beams directed towards a projection axis of the dental light. The at least one cure-safe illuminator is configured to produce a cure-safe beam directed towards the projection axis of the dental light. The at least one cure-safe illuminator can be configured to substantially reduce transmission of light by the cure-safe illuminator having a wavelength below about 500 nanometers. The at least one cure-safe illuminator can comprise at least one collimating lens that is dyed so as to reduce transmission of light having a wavelength below about 500 nanometers through the at least one collimating lens.

According to another embodiment, a dental light comprises a plurality of normal-mode illuminators arranged approximately equidistant from a central point to define a substantially circular array and at least four cure-safe illuminators arranged equidistant from the central point and outside of the substantially circular array. The central point can be located along a projection axis of the dental light. Each normal-mode illuminator can be configured such that the respective normal-mode beams each form an angle with the projection axis that is greater than zero but less than 10 degrees, or that is between about 4 and about 5 degrees. Each cure-safe illuminator can be configured such that the respective cure-safe beams each form an angle with the projection axis that is greater than zero but less than 15 degrees, or that is between about 6 and about 8 degrees.

According to another embodiment, a dental light comprises a rear housing, a plurality of LED light sources arranged in a substantially symmetric array about a central point and coupled to the rear housing, and a pivot assembly attached to the rear housing at the central point. The central point corresponds substantially to the center of mass of the dental light. The pivot assembly can comprise a pivot arm capable of rotational motion into a recess formed in the rear housing. The recess can be situated between a first and a second of the plurality of LED sources and formed such that the pivot arm fits into the recess at a lower rotational limit. The pivot assembly can comprise an adjustable tension forked pivot bracket. The dental light can further comprise a front housing and a front shield secured to the front housing. The front housing is attached to the rear housing such that the plurality of LED light sources occupy an area between the front and the rear housing. The front housing can have a trough along at least a portion of its perimeter. The dental light can further comprise a flexible gasket received in the trough, where the gasket serves to seal the connection between the shield and the front housing.

In one example, the dental light comprises at least one handle secured to the front housing to facilitate positioning of the dental light. The at least one handle has a rigid interior structure covered at least partially with a flexible tactile material. The flexible tactile material can have a Shore A durometer of less than about 95 and the rigid interior structure can have a Shore A durometer of greater than about 95. The rigid interior structure of the handle can be formed by shaping a rigid thermoplastic substrate and the flexible tactile material can be a flexible thermoplastic that is molded over the rigid interior structure. The flexible tactile material can have a Shore A durometer of between about 70 and about 95 and the rigid interior structure can be an engineered resin.

According to another embodiment, a dental light comprises a housing unit, a circuit board shaped to fit within the housing unit and be secured to the housing unit, a plurality of light emitting diode (LED) light sources coupled to the circuit board, and an LED driver. The plurality of the LED light sources comprises a first set of LED light sources dedicated to normal mode operation and a second set of LED light sources dedicated to cure-safe mode operation. The first and the second sets are electrically independent. The LED driver is electrically coupled to the first and the second set of LED light sources via the circuit board and comprises a first and a second output. The LED driver is capable of supporting both the normal and cure-safe modes of operation by communicating with the first set via the first output and communicating with the second set via the second output. The LED driver can comprise a buck-boost current regulator.

According to another embodiment, a dental light comprises a housing unit, a circuit board shaped to fit within the housing unit and secured to the housing unit, a plurality of light emitting diode (LED) light sources coupled to the circuit board, a communications interface, and a cable. The communications interface is configured to receive control information from a user and to transmit data using a controller-area network (CANbus) system. The cable is capable of transmitting the data and of providing power to the LED light sources. The circuit board can be coupled to at least one LED driver in communication with the plurality of LED light sources, and the CANbus system can be configured to transmit messages to and to receive messages from the at least one LED driver.

The foregoing and additional features and advantages will be more readily apparent from the following detailed description, which proceeds with reference to the accompanying figures.

BRIEF DESCRIPTION OF THE DRAWINGS

FIG. 3 is an exploded perspective view showing select component parts of one specific implementation of the LED dental light of FIG. 1.

FIG. 11A is an elevation view of an exemplary shield to be used with an LED dental light.

FIG. 11B is a cross-sectional view taken along the line 11B-11B in FIG. 11A.

FIG. 11C is a cross-sectional view taken along the line 11C-11C in FIG. 11A.

FIG. 11D is an enlarged view of the region 11D in FIG. 11C.

FIG. 12 is an elevation view of another specific implementation of the LED dental light of FIG. 1.

FIG. 13 is a cross-sectional view taken along the line 13-13 in FIG. 12.

FIG. 14 is an enlarged view of the region 14 in FIG. 13.

FIG. 15 is a perspective view of a rear portion of an LED dental light.

FIG. 16 is an exploded perspective view of the component parts of an exemplary pivot assembly.

DETAILED DESCRIPTION

Figure 1:
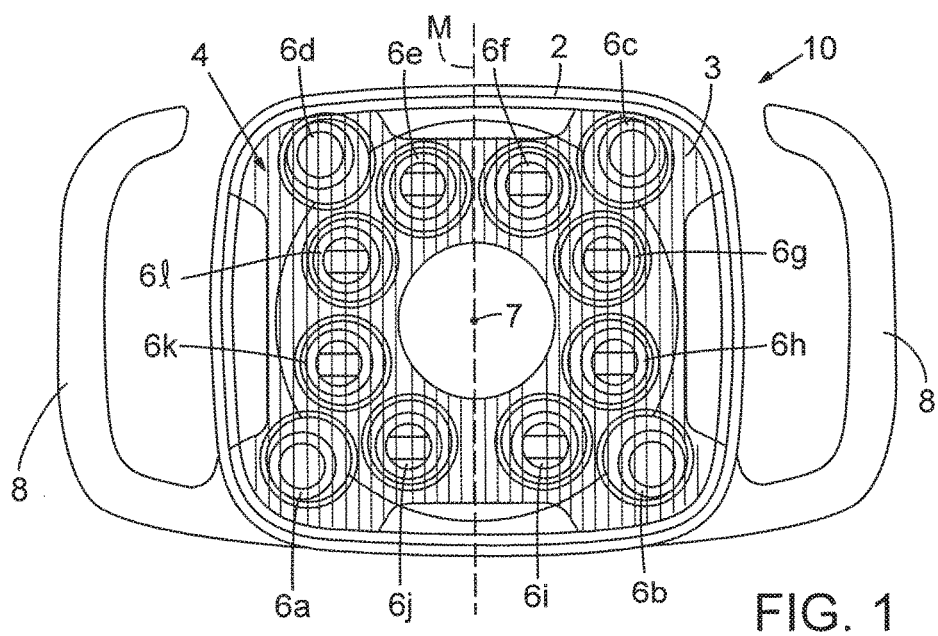
FIG. 1 is an elevation view showing a front side of an exemplary LED dental light.

Referring to the drawings, and more specifically to FIG. 1, an embodiment of an LED dental light 10 is illustrated. In FIG. 1, the LED dental light 10 comprises a housing 2 and several illuminators 6a-6l. The illuminators 6a-6l comprise LED light sources and various optics for modifying and shaping light emitted from the LED light sources. For example, each of the illuminators 6a-6l can comprise an LED light source and a collimating lens system, or other optics as described herein. In the illustrated embodiment, the illuminators 6a-6l are arranged in a substantially symmetric pattern around a central point 7, and are symmetric with respect to a line M passing through the point 7. However, other arrangements of illuminators are possible. For example, illuminators can be arranged in other symmetric or asymmetric patterns. Also, although FIG. 1 illustrates a particular number of illuminators, more or fewer illuminators may be used depending on the desired luminous output of the LED dental light. In general, the light emitted by the LED dental light should be sufficiently bright to allow dental diagnosis and treatment.

The illuminators 6a-6l are positioned behind a shield 4 within the housing 2. In the illustrated embodiment, the shield 4 comprises an array of cylindrical lenses 3 and performs a shaping function on the light emitted from the illuminators 6a-6l. As shown, each of the illuminators 6a-6l transmits light through more than one of the cylindrical lenses 3. The LED dental light 10 also has two handles 8 secured to the housing 2 to facilitate positioning of the LED dental light 10 by a dentist, dental assistant or other user. The housing 2 of the LED dental light 10 can be mounted to a flex arm or other structure (see, for example, FIGS. 17-18). In that manner, the light can be positioned such that the illuminators 6a-6l illuminate a desired area of a dental patient, typically an area within the oral cavity of the patient.

Figure 20:
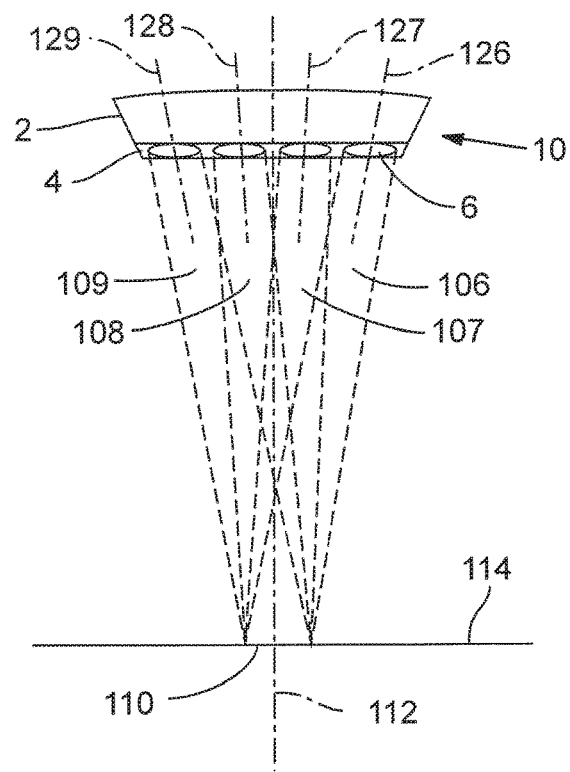
FIG. 20 is a schematic showing the illumination produced by the LED dental light of FIG. 1.

Referring to FIG. 20, the LED dental light 10 is shown illuminating an area 110 contained within an illumination plane 114. For purposes of illustration, only four illuminators 6 are shown. The illuminators 6 are shown producing light beams 106, 107, 108, 109 parallel to and along respective illumination axes 126, 127, 128, 129. The illuminators 6 can be configured such that the light beams 106, 107, 108, 109 produce beam patterns at the illumination plane 114. The light beams 106, 107, 108, 109 substantially overlap at the area 110, which can be referred to as an illumination area. In order that the light beams 106, 107, 108, 109 substantially overlap at the area 110, the corresponding illumination axes 126, 127, 128, 129 are directed towards an axis 112.

The axis 112 intersects the illumination plane 114 within the area 110 and can be referred to as a projection axis of the LED dental light 10. The projection axis of an LED dental light is generally defined by the direction of the light it emits. Therefore, the projection axis can be drawn between the LED dental light and the area illuminated by the LED dental light. In some embodiments, the projection axis can be a central axis of the LED dental light. For example, the LED dental light 10 can have a projection axis that passes through, or near to, the central point 7.

In some embodiments, the illumination plane 114 corresponds to a focal plane of the light beams 106, 107, 108, 109. Generally, a focal plane can be the plane where light beams produced by a plurality of illuminators substantially overlap to produce a composite pattern of minimum size. Typically, the illumination plane 114 is located at between 550 and 850 millimeters from the LED dental light 10. In some examples, the illumination plane can be located between about 700 mm and 750 mm from the LED dental light, or approximately 700 mm from the shield 4 of the LED dental light 10. During use in a dental setting, the LED dental light 10 is desirably positioned such that the oral cavity of the patient is within the area 110.

Figure 19:
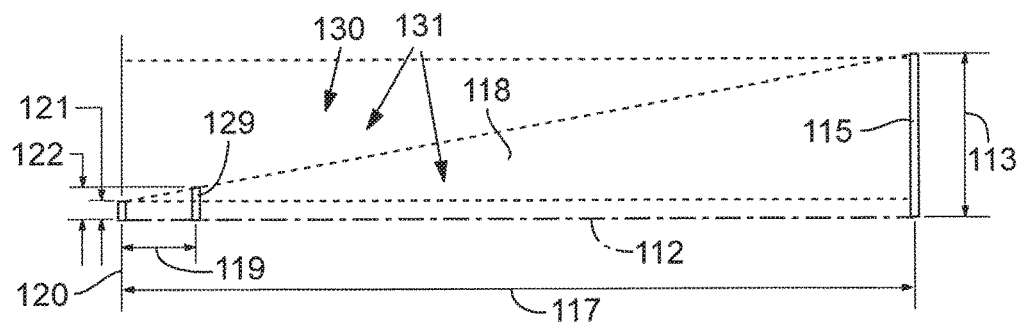
FIG. 19 is a schematic showing the illumination produced by an exemplary LED dental light.

In dental applications, it is typically desired that the illumination plane be located at a predetermined distance based on standards within the industry. For example, ISO 9680:2007 is a standard for dental lights. This standard requires that the hard shadow generated by a disk having a diameter of 20 mm located at 50 mm from the illumination plane, positioned 700 mm from the dental light, be no greater than 12 mm in any dimension. Satisfaction of this standard can be demonstrated by reference to FIG. 19. In the figure, a light source 115 having a projection axis 112 is shown. For purposes of illustration, only approximately half of the light source 115 is shown, the light source 115 being divided along its projection axis 112. The radius of the light source 115 is shown as distance 113. The light source 115 produces a light beam 131 that is incident on a disk 129 located at a distance 119 from an illumination plane 120, the disk having a radius 122. Light rays confined entirely within the part of the light beam labeled 118 are blocked from reaching the illumination plane 120 by the disk 129, while rays extending into the part of the light beam labeled 130 are not blocked by the disk 129 and reach the illumination plane. Applying the ISO 9680:2007 standard, the radius 122 of the disk 129 is 10 mm, and the distance 119 is 50 mm. A hard shadow is shown at the illumination plane 120 having a radius 121, and the hard shadow is located at a distance 117 from the light source, which is approximately 700 mm.

In order to satisfy the ISO 9680:2007 standard, the hard shadow radius 121 must be no greater than 6 mm. LED dental lights described herein satisfy this standard. For example, in one implementation, the LED dental light has a radius 113 of 62 mm, where the radius represents the outer edge of collimating lens systems used in the LED dental light. That is, the collimating lens systems are arranged along a circle with a diameter of 124 mm, such that the collimating lens systems are touching but within the circle.

In such an implementation, the hard shadow is less than 12 mm in diameter. In other implementations, the LED dental light has a radius 113 that is greater than 62 mm while still maintaining a hard shadow that is not greater than 12 mm in any dimension.

In general, as the radius 113 of the light source 115 is increased, the dental light may have increased position sensitivity. That is, the beam pattern size can become more sensitive to changes in the distance between the light source and the illumination plane. For example, small changes in this distance can produce large variations in the beam pattern size. It is generally desirable to reduce sensitivity because position sensitivity makes the dental light difficult to position by the user so as to provide a desired illumination of the patient. Thus, the size of the LED dental light can be chosen to balance reduction in hard shadow size against increasing position sensitivity.

Another concern for dental light design is to provide users with the option to alter the spectral power distribution of the dental light when preparing and/or applying light-curable dental materials. Thus, LED dental lights described herein can, in some implementations, be operated as dual-mode LED dental lights. That is, the LED dental light can be operated in two modes: a normal mode and a mode compatible or safe for use with light-curable dental materials, also described herein as a "cure-safe" mode. In the normal mode, the LED dental light emits white colored light for general use in a dental setting. In the cure-safe mode, the LED dental light emits light that is substantially free of wavelengths of light associated with the photo-initiated reaction of light-curable dental materials and does not appreciably initiate premature curing of the dental material. It is preferable for a dentist to operate in the cure-safe mode when light-curable dental materials are being used. For example, such materials are frequently used in dental restoration procedures as well as for sealants, varnishes, and orthodontia bracket bonding. This mode enables the operator to illuminate the oral cavity of a patient while utilizing a light-curable dental material in the illuminated area with reduced risk of premature curing of the material by the dental light.

More specifically, light-curable dental materials contain photo-initiators, which absorb certain wavelengths of light and start a polymerization of a resin monomer. A commonly used photo-initiator is Camphorquinone, which has a light absorption peak around 469 nm. Other photo-initiators typically have a similar or sometimes lower absorption peak (e.g., Phenylpropanedione and Lucirin TPO). In order for dentists to use light-curable dental materials under the illumination of an LED dental light and also avoid premature polymerization, the LED dental light can be operated in the cure-safe mode. That is, the LED dental light can be configured to reduce emission close to the polymerization wavelength when a cure-safe beam is desired. For example, in some implementations described herein, the LED dental light contains illuminators that are designed to function only in the cure-safe mode (cure-safe illuminators) and illuminators that are designed to function only in the normal mode (normal-mode illuminators). When the LED dental light is placed in cure-safe mode, only the cure-safe illuminators are activated. When the LED dental light is placed in normal mode, only the normal-mode illuminators are activated.

In general, cure-safe illuminators are configured to reduce the emission of light below the wavelength of 500 nm to reduce premature polymerization of the light-curable dental materials. However, a person of skill in the art would understand that this wavelength should be selected based on the particular material being used in the dental procedure. The emission of light from the cure-safe illuminators can be modified through use of a band pass filter known in the art. For example, a filter can be incorporated into the optics within the illuminator. In some embodiments, the cure-safe illuminator includes a collimating lens system with a filter. For example, the collimating lens system can include one or more lenses that are tinted or dyed so as to reduce transmission of light having a wavelength of about 500 nm or less.

Figure 6:
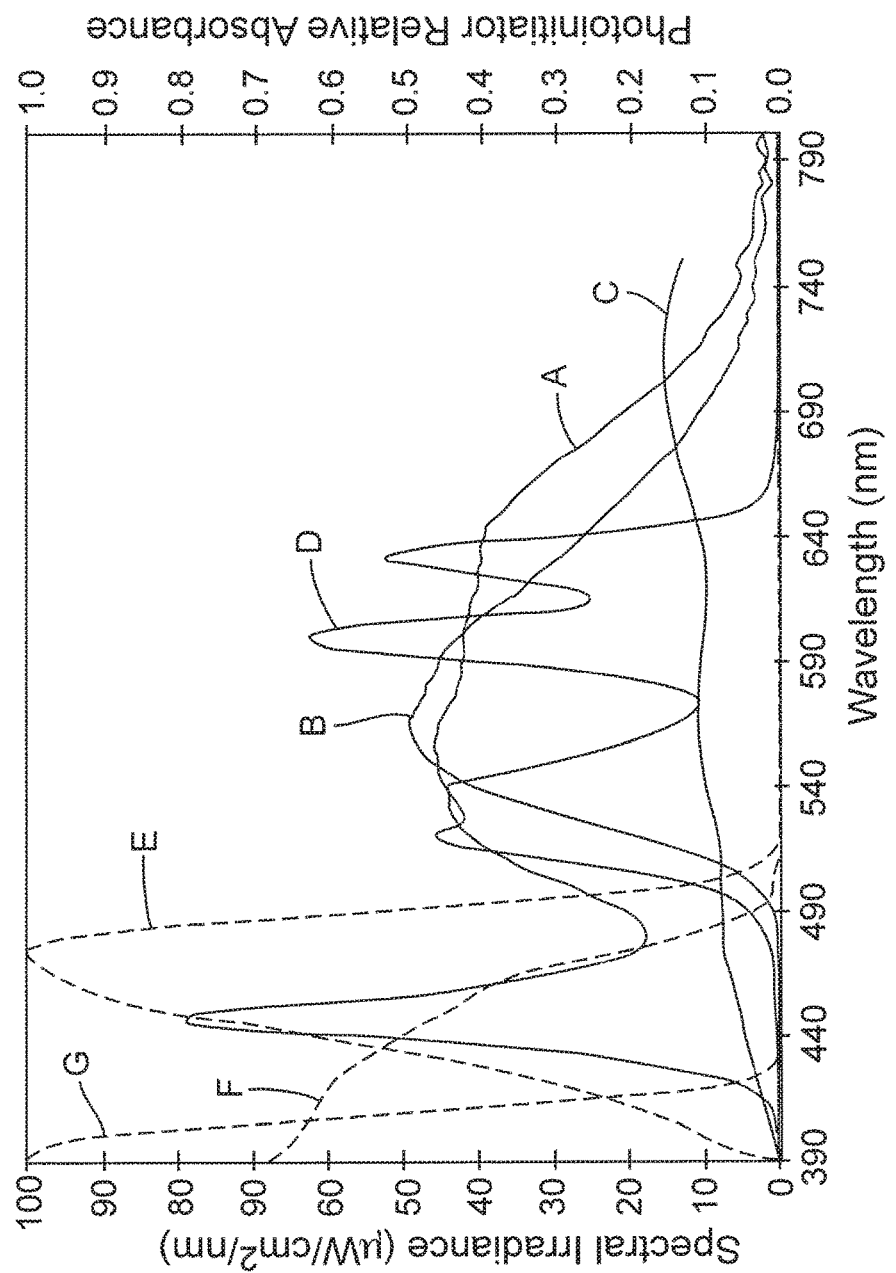
FIG. 6 is a plot showing absorption spectra for photoinitiators and emission spectra for several dental lights.

Referring to FIG. 6, light absorption is plotted versus wavelength for three different photo-initiators represented by lines E, F, G. As shown, all three photo-initiators demonstrate absorption peaks at wavelengths of 500 nm or less. Line A represents an emission spectrum for an example LED dental light in accordance with this disclosure operating in normal mode. As shown, the LED dental light emits light at a range of wavelengths, including below 500 nm. Thus, emission line A can be referred to as white light emission. Line B represents the emission spectrum for an exemplary LED dental light in accordance with this disclosure and operating in a cure-safe mode. As shown, this LED dental light has significantly reduced emission of light below 500 nm. Line C represents the emission spectrum for a conventional tungsten-halogen dental light, operated at its lowest intensity setting to minimize blue light. As shown, this type of dental light exhibits a significant amount of blue light even when operating in this mode. Line D represents the emission spectrum for a multi-color LED source in a conventional dental light where the blue LED source is turned off. As shown, this light still emits some light below 500 nm, and therefore may not be as effective during dental applications using light-curable dental materials as the LED dental light represented by line B. Comparing the dental light emission spectra of lines A, C and D to the photo-initiator represented by line E, the lines A, C and D overlap line E significantly more than line B. As a result, more premature polymerization will result with the lights represented by lines A, C and D than with the light represented by line B.

Referring to FIG. 1, the LED dental light 10 can be implemented as a dual-mode light. For example, the illuminators 6a, 6b, 6c, 6d can be cure-safe illuminators and arranged as shown in an approximately square array. That is, the four cure-safe illuminators can be positioned approximately equidistant from the central point 7. Also, the illuminators 6e, 6f, 6g, 6h, 6i, 6j, 6k, 6f can be normal-mode illuminators and arranged as shown in an approximately circular array. In some embodiments, the illuminators 6e, 6f, 6g, 6h, 6i, 6j, 6k, 6E are located along a circle with a diameter of between approximately 100 and 150 mm. In one embodiment, a diameter of the illuminator is approximately 32 mm and the centers of the LED light sources contained within the illuminators are located along a circle with a diameter of approximately 108 mm or greater. However, other arrangements of cure-safe and normal-mode illuminators are possible. For example, illuminators, whether cure-safe or normal-mode, can be arranged along any polygon shape or in other symmetric or asymmetric distributions. In general, the positions of the illuminators and the spacing between the illuminators can be selected to keep the size of the dental light small while also reducing hard shadows (which can favor a larger distribution and tight spacing between illuminators) and position sensitivity.

Figure 7A:
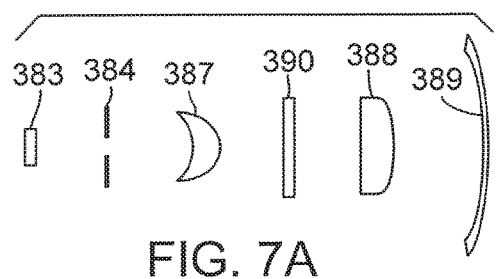
FIG. 7A is a schematic of an optical system representing an exemplary normal-mode illuminator.

In such a dual-mode implementation, the normal-mode illuminators and the cure-safe illuminators can include optics configured for the illuminator's desired function. For example, a schematic of an optical system representing an exemplary normal-mode illuminator is shown in FIG. 7A. In the figure, an LED light source 383 is configured to produce a light beam that is received by an aperture 384, which functions to shape the received light beam. Downstream from the aperture 384 is a lens 387, which performs a collimating and collecting, or condensing, action on the received light beam. Downstream from the lens 387 is a diffuser 390, which functions to mix light within the received light beam to increase color uniformity of the beam. Downstream from the diffuser 390 is a lens 388, which performs a collimating, or condensing, action on the received beam. Downstream from the lens 388 is a shaping lens 389. As implemented in FIG. 1, the shaping lens 389 function is performed by the shield 4. However, the shaping lens can be a separate optical element or set of optical elements.

Figure 7B:
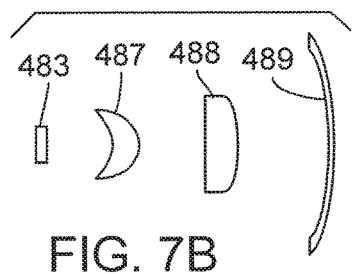
FIG. 7B is a schematic of an optical system representing an exemplary cure-safe illuminator.

In addition, a schematic of an optical system representing an exemplary cure-safe illuminator is shown in FIG. 7B. In the figure, an LED light source 483 is configured to produce a light beam that is received by a lens 487, which performs a collimating, or condensing, action on the received light beam. Downstream from the lens 487 is a lens 488, which also performs a collimating, or condensing, action on the received light beam. As an exemplary cure-safe illuminator, the optical system of FIG. 7B includes a mechanism for producing a cure-safe light beam, as described above. For example, the lens 488 and/or 487 can be tinted or dyed so as to substantially reduce transmission of light having a wavelength below about 500 nm. Alternatively, an additional optical element, such as a color tinted or dyed color filter, can be added to the illustrated optical system to filter transmitted light. Downstream from the lens 488 is a shaping lens 489. As implemented in FIG. 1, the shaping lens 489 function is performed by the shield 4. However, the shaping lens can be a separate optical element or set of optical elements.

As will become more apparent from the description below, normal-mode illuminators and cure-safe illuminators can include optical systems different from those shown in FIGS. 7A and 7B. Further, the optics shown in FIGS. 7A and 7B, along with their functions and alternatives, will be described in more detail below.

FIG. 3 is an exploded view showing a specific implementation of the LED dental light of FIG. 1. FIG. 3 illustrates component parts of the LED dental light 70. The component parts are expanded along a central axis 9, which in some implementations can also be a projection axis of the LED dental light 70. A rear housing 50 forms of rear portion of the LED dental light 70. The rear housing 50 can be made from various materials known in the art, such as various metals and plastics. The rear housing 50 can include a recess 51 and a central area 52. In some implementations, a pivot assembly (not shown, but see below at FIGS. 15-16) is attached to the rear housing at the central area 52. The pivot assembly can include a pivot arm that can rotate to fit within the recess 51. The central area 52 can be located at an approximate center of mass of the LED dental light 70.

A substrate 30 can be mounted to the rear housing 50. The LED light sources (not shown) are mounted to the substrate 30. The substrate 30 can also include or be connected to various electronics for controlling the LED light sources. The substrate 30 can be any printed circuit board known in the art, or other material used as a substrate for LED light sources. Because LED light sources generate heat when activated, in some implementations, the substrate 30 and the rear housing 50 can be configured so as to facilitate heat removal from the dental light 70. For example, the rear housing 50 can be a cast metal housing, and the substrate 30 can be a thermally conductive printed circuit board, such as a printed circuit board with an aluminum, copper, or other thermally conductive substrate, a dielectric layer and a circuit layer. The substrate 30 can be mounted directly to the rear housing 50 so as to provide direct thermal contact between the substrate 30 and the rear housing 50. In some examples, the substrate 30 can be mounted to the rear housing 50 with thermally conductive grease, compound, pads, or other material at the location of each LED light source on the substrate 30 to further facilitate heat transfer. In some examples, the heat produced by the LED light sources can be dissipated from the LED dental light 70 without the need for active cooling or air vents in the dental light. Avoiding air vents can enable the LED dental light 70 to be a fully enclosed optical system and circuit board, if desired. Such a fully enclosed system can reduce contamination and damage to the optical and electrical components from dust, fluids, or cleaning chemicals.

Further explaining FIG. 3, lens modules 40 are coupled to the substrate 30. Generally, one lens module 40 can be coupled to the substrate 30 for each LED light source mounted to the substrate 30. Each lens module 40 can be positioned to receive the light beams produced by respective LED light sources. Each lens module 40 comprises optics described herein to modify and shape the received light beam. For example, the lens modules 40 can include optics to collect, collimate, and/or condense the light beams emitted from the LED light sources. However, other optics can also be used in the lens modules 40.

The lens modules 40 can be mounted to the substrate 30 using optical bases 31, 32, 33, 34, which can be mounted to the substrate 30, e.g., with screws or other fasteners. For example, the lens modules 40 can twist and lock into the bases 31, 32, 33, 34. In general, the optical bases 31, 32, 33, 34 function as an intermediary structure to facilitate coupling of the lens modules 40 to the substrate 30. Thus, other structures can be used in place of the optical bases to perform this function. Alternatively, the lens modules 40 can be mounted directly to the substrate 30 without use of an optical base or other intermediary structure.

An optional front housing 54 fits over the lens modules 40 and is secured to the rear housing 50. The front housing 54 is typically formed so that it does not obstruct light transmitted through the lens modules 40. For example, the front housing 54 can be situated such that each of the lens modules 40 corresponds to a hole 55. The front housing 54 can also act as a decorative mask for the optics used in the LED dental light 70.

Handles 8 can be attached to the front housing 54, or alternatively to the rear housing 50, by any suitable approach, such as by using screws 56 or other fasteners, and can be removable. For example, the handles 8 can be mounted by a quick release, non-tooled connection to allow the handles to be disconnected and separately run through a dishwasher or sterilizer. In general, the handles 8 can be large, ergonomic grips with a rubberized grip surface which allows the user to move the LED dental light 70 with ease and reduced hand strain. The handles 8 can have a rigid interior structure covered at least partially with a flexible tactile material. The rigid interior structure can be formed by shaping a rigid thermoplastic substrate. The substrate can be a high strength engineered resin, which can have a mineral fill, glass fill, or other fill for increased rigidity. The flexible tactile material can be a thermoplastic that is molded over the rigid interior structure. In some embodiments, the flexible tactile material has a Shore A durometer of less than 95, and the rigid interior structure has a Shore A durometer of greater than 95. Further, in some examples, the flexible tactile material has a Shore A durometer of between about 70 and 90. The handles 8 can be horn-shaped with curved ends 5 on the top to allow the use of slip-on asepsis barriers (not shown). This shape, as well as the rubberized surface, can help prevent the barriers from slipping off during use.

Decorative features 60, 61, 62 are optionally mounted to the front housing 54, if present, or to the rear housing 50 if the optional front housing is not present. For example, the decorative features 60, 61, 62 can be labels that when applied hide fasteners such as screws used to secure together the component parts of the LED dental light 70. In this manner, the fasteners are no longer visible from the exterior of the LED dental light 70, and the fasteners no longer act as collection areas for contaminants.

The front shield 4 is then secured to the front housing 54, if present, or to the rear housing 50 if the optional front housing is not present. For example, the front shield 4 may have an integrated snap feature that allows the shield to snap on to the front housing 54. The shield 4 is made of a transparent material, and can function as a dust shield. The shield 4 can be flat with smooth edges that wrap over a portion of the front housing 54. A flexible gasket 57 can be fitted in a trough 53 around the perimeter of the front housing 54. Alternatively, the shield 4 can include a trough or both the front housing 54 and the shield 4 can include the trough. In this manner, the shield 4 can be sealed against the front housing 54. Such a seal can make the LED dental light 70 easier to clean by protecting the lens modules 40 and any electronics connected to the substrate 30 from damage caused by water or cleaning chemicals. Thus, the shield 4 can reduce the need to remove components of the LED dental light 70 in order to clean them. Alternatively, the shield can be flat and secured to the dental light by an adhesive bond or by a bezel wrapping over the front face of the shield with or without a seal.

The front shield 4 is shown in FIG. 3 without an array of lenses 3 (see FIG. 1), which perform a final shaping function on received light beam(s). If such shaping is desired, shaping lenses can be included as separate elements from the shield 4. For example, shaping lenses can be included in the modules 40. However, in some embodiments, the shield 4 can also serve a light shaping function. For example, an array of shaping lenses can be mounted to the shield 4, or an array of lenses can be integrated into an inner or outer surface of the shield 4.

Figure 2:
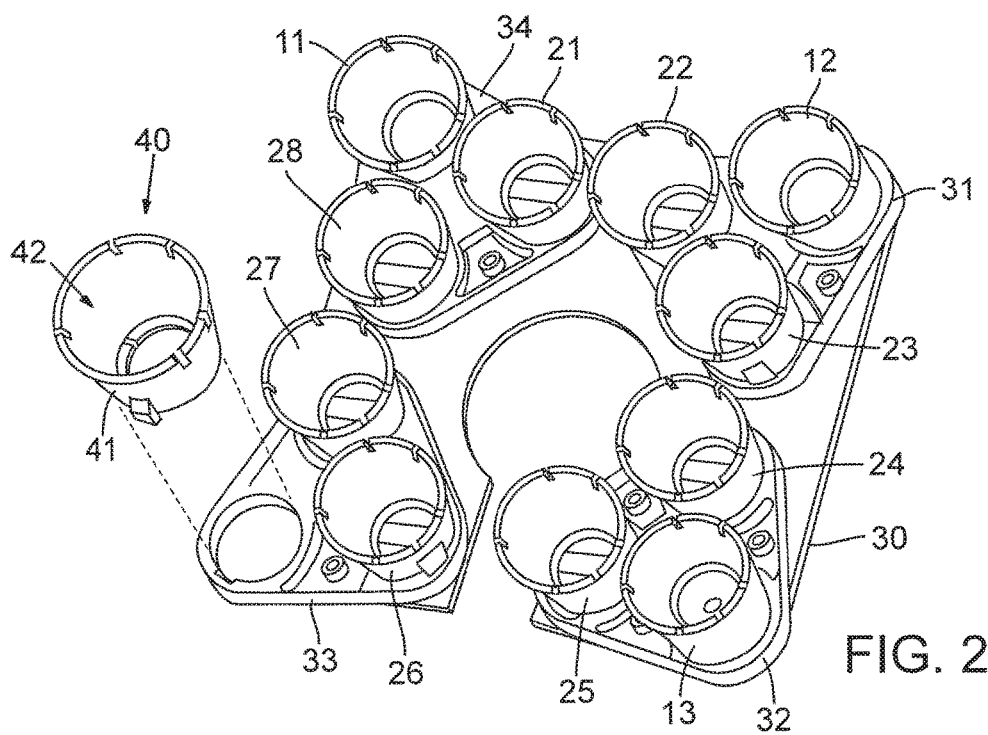
FIG. 2 is a perspective view of select component parts of the LED dental light of FIG. 3.

FIG. 2 provides an enlarged view of individual lens modules mounted to bases 31, 32, 33, 34 of the LED dental light of FIG. 3. In the figure, lens module 40 is shown to include a lens housing 41, which holds in place various optics 42 such as, e.g., a collimating lens system and/or other optics as shown in FIGS. 4, 5 and 7-9 and described herein. For clarity, the optics are not shown in FIG. 2, and the region 42 represents the space in which the optics are located. In the figure, lens modules 11, 21, 28 are mounted to the base 34. Further, lens modules 12, 22, 23 are mounted to the base 31, lens modules 13, 24, 25 are mounted to the base 32, and lens modules 40, 26, 27 are mounted to the base 33. The bases 31, 32, 33, 34 are then mounted to the substrate 30. LED light sources (not shown) are mounted to the substrate 30 such that each lens module corresponds to an LED light source.

FIGS. 4 and 5 provide additional views of exemplary lens modules and optics contained therein. Specifically, FIG. 4A is an elevation view of an exemplary lens module 80 and LED light source 83, with an aperture 84 having a substantially rectangular shape. As shown, the lens module 80 includes a lens housing 81 and optics 82 held in place by the housing 81. For clarity, the optics 82 are not shown in FIG. 4A. FIG. 4B is a cross-sectional view of the lens module 80 and LED light source 83, and illustrates exemplary optics 82. The lens curvatures and spacing between optical elements shown in FIG. 4B are schematic and not drawn for scale. For purposes of illustration, the lens housing 81 is not shown, and the aperture 84 is shown to be included in the optics 82. The aperture 84 can be part of an optical base to which a lens module is mounted, or the aperture 84 can be part of the optics in a lens module and held in place by the lens housing.

Figure 4A:
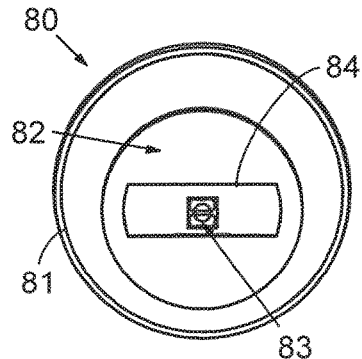
FIG. 4A is an elevation view of an exemplary lens module and LED light source.
Figure 4B:
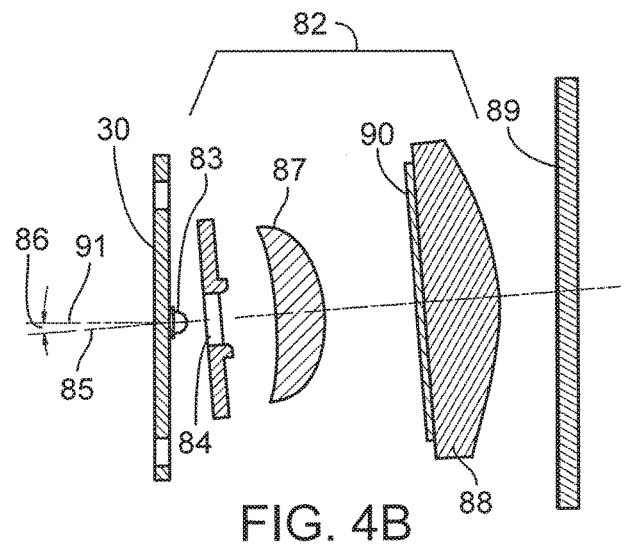
FIG. 4B is a cross-sectional view of a shaping lens and the lens module and LED light source of FIG. 4A.

In FIG. 4B, the LED light source 83, mounted to the substrate 30, is configured to produce a light beam that is received by optics 82, which include lenses 87 and 88, and then received by shaping lens 89. The optics 82 represent an exemplary collimating lens system. Thus, the optics 82 can be referred to as a collimating lens system. However, a collimating lens system can include fewer or more optics than the optical system 82. In general, a collimating lens system includes at least one optical element, such as one or more lenses, configured to perform collimating action on a received light beam. A collimating lens system can also function to collect and/or condense light. A collimating lens system can include other optics in addition to those capable of performing collimating, collection, or condensing action. Such other optics include lenses and other devices known in the art, or described herein, for shaping, mixing, filtering, focusing or otherwise modifying light. The components of a collimating lens system are typically transmissive, i.e., the components transmit rather than reflect the majority of received light. The components of a collimating lens system can be selected so as to produce the desired beam pattern at the illumination plane of the LED dental light.

Referring to FIG. 4B, an axis 85 defines an optical axis of the optics 82 and intersects the optics 82 at an approximate center. The axis 85 can be referred to as an illumination axis when it is parallel to and directed along the direction of propagation of light emitted from the optics 82 or the lens module 80. In the illustrated implementation, the axis 85 is shown to be displaced from an axis 91 by an angular displacement 86. The axis 91 corresponds to a normal axis of the LED light source 83. That is, the axis 91 is perpendicular to the substrate 30 at an approximate center of the LED light source 83. Preferably, the illumination axis 85 intersects axis 91 at the approximate center of the LED light source 83.

In general, the angular displacement 86 can be selected to generate a desired illumination by the LED dental light at the illumination plane. For example, if the LED dental light includes more than one LED light source and collimating lens system, the angular displacement 86 for each lens system can be selected such that the light beams transmitted through each lens system substantially overlap at the illumination plane of the LED dental light. For example, the angular displacement 86 for each collimating lens system can be selected such that respective illumination axes are directed towards the propagation axis of the dental light. In some embodiments, the angular displacement 86 is approximately zero. In other embodiments, the angular displacement 86 is greater than zero but less than 15 degrees. In some embodiments, the angular displacement 86 is between 4 and 5 degrees, while in other embodiments the angular displacement 86 is between 6 and 8 degrees. In a particular embodiment, the angular displacement 86 is about 4.5 degrees, while in another particular embodiment the angular displacement 86 is about 7 degrees. Each collimating lens system of an LED dental light can have the same angular displacement or the lens systems can have a variety of different angular displacements.

Figure 4C:
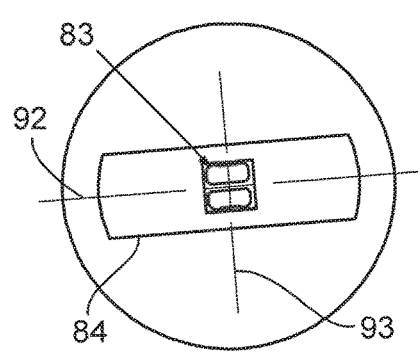
FIG. 4C is an elevation view of an enlarged portion of the lens module and LED light source of FIG. 4A.
Figure 4D:
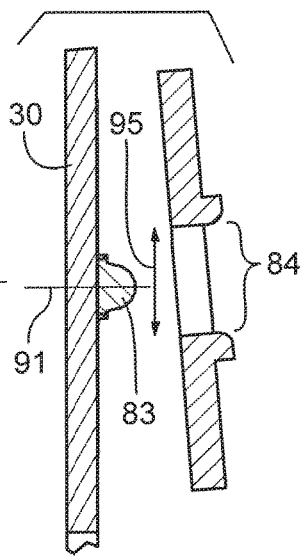
FIG. 4D is an enlarged view of the LED light source and aperture of FIG. 4B.

Referring to the optics 82 in FIG. 4B, the light beam produced by the LED light source 83 is received first by the aperture 84. FIG. 4C is an enlarged view of a portion of the lens module 80 and LED light source 83, and shows the aperture 84 having a short axis 93 and a long axis 92. FIG. 4D is an enlarged view of the LED light source 83 and the aperture 84. The LED light source is desirably a white light source, and can be any LED light source known in the art. In some implementations, the LED light source is a high bright white LED with a domed aspheric lens. When high quality of light is desired (to be explained further below), exemplary LED light sources can include those which have qualifying parameters such as Correlated Color Temperature (CCT) of about 5000 Kelvin, single-chip construction, a Color Rendering Index (CRI) greater than 80, and International Commission on Illumination (CIE) chromaticity coordinates close to the Planckian black body locus (as measured when the LED light source is incorporated into the LED dental light).

Components that exhibit such parameters are available from, for example, Phillips, Everlight, Nichia, and others and can be selected from Nichia's NCSW119, NCSW219, NVSW119, and NVSW219 series of LEDs, as just some examples. Of course, other equivalent LEDs could also be used.

The light produced by the LED light source 83 can be described as a light beam propagating along the normal axis 91 away from the substrate 30. In general, an LED light source emits light in many different directions. Thus, the light beam produced by an LED light source contains light having a plurality of angles of propagation measured relative to the normal axis 91. These angles of propagation can be referred to as an angular distribution of the light beam. When the light beam emitted from the LED light source 83 is transmitted through the aperture 84, the angles of propagation of the light in the light beam are reduced based on the shape of the aperture. In FIG. 4D, the angular distribution of the light is reduced along an axis 95, which is perpendicular to the normal axis 91. In this manner, the aperture 84 functions to shape the light beam emitted from the LED light source 83. The axis 95 corresponds to the short axis 93 of the aperture 84. However, in the implementation shown in FIG. 4D, the axis 95 is not parallel to the short axis 93 of the aperture 84 because the angular displacement 86 of the optics 82 is non-zero. In some embodiments, the axis 95 may be parallel to the short axis 93 of the aperture 84.

Figure 9:
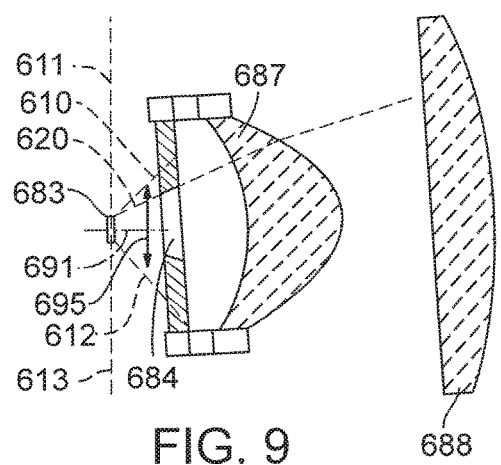
FIG. 9 is a cross-sectional view of an exemplary lens system with an aperture.

FIG. 9 further illustrates this shaping function of an aperture. FIG. 9 is a cross-sectional view of an exemplary lens system with an aperture 684. Lines 610, 611, 612, 613, 620 represent rays of light propagating from the LED light source 683. The area between lines 611 and 613 represents an angular distribution of the light beam emitted from the LED light source 683. The angles of propagation of the light in the light beam can be measured from the normal 691, which is perpendicular to the LED light source 683 at an approximate center. As shown in the figure, the aperture 684 accepts the light ray 620, which is received by the lens system comprising lenses 687 and 688, while the light rays 610 and 612 are rejected by the aperture 684 and are not received by the lens system. In this manner, the aperture 684 functions to reduce the angular distribution of the light emitted from the LED light source 683 along an axis 695 that is perpendicular to the normal 691.

Referring back to FIGS. 4A-4D, the illustrated aperture has an obround shape with straight sides and rounded ends. Although the aperture 84 is substantially rectangular in shape, the aperture 84 can have a different shape. For example, the aperture 84 can be more or less rectangular, or more or less oval, in shape. The aperture 84 can be symmetric or asymmetric. Further, the edges of the aperture can be flat or angled. Compare, for example, aperture 84 of FIG. 4D to aperture 684 of FIG. 9. Angled edges may be helpful for reducing reflection of light off the aperture, causing stray light outside of the desired illumination pattern of the dental light. In general, the size, shape and position of the aperture 84 can be selected so as to reduce patient eye glare. A light beam transmitted through a rectangular-shaped aperture can create an oval or rectangular-shaped beam pattern at the illumination plane. Because a patient's eyes are located fairly close to the oral cavity, it is desirable for dental lights to emit light that is shaped so as to reduce light directed toward the eyes and thereby reduce eye glare. For example, when the illuminated region corresponds to the patient's oral cavity, the ISO 9680:2007 standard requires that the illuminance at 60 mm from a center of the illuminated region along the illumination plane (and towards the patient's eyes) be less than 1200 lux. The shape of the aperture 84 can be chosen so as to satisfy this standard such as by further reducing the light in the direction of the patient's eyes. Additionally, the position of aperture 84 relative to the optics 82 can be selected so as to achieve a desired beam pattern shape at the illumination plane.

In general, the aperture 84 is an optional element that may or may not be included in the lens module 80 or in optics 82. Thus, illuminators described herein may or may not include such an aperture. Typically, the aperture 84 is included in a normal-mode illuminator. A cure-safe illuminator may not include an aperture 84 when the eye glare problems described above are not significant.

Referring to FIG. 4B, after the light is shaped by the aperture 84, it is received by lens 87. Lens 87 can be any aspherical collector lens or other collection element. For example, lens 87 can be a custom designed molded acrylic, polycarbonate, glass or other suitably transparent lens. In general, lens 87 acts as a collection element to perform collimating action on a received light beam. Downstream from lens 87 is lens 88. Lens 88 can be any plano-convex collimator lens, Fresnel lens or other collimating lens. For example, lens 88 can be a custom designed molded acrylic, polycarbonate, glass or other suitably transparent lens providing secondary collimation on a received light beam. Together, lens 87 and lens 88 provide desired collection, collimation, and/or condensing of the light emitted from the LED light source 83 and transmitted through the aperture 84. In general, lens 87 and lens 88 can be selected to produce a desired beam pattern at a desired distance from the LED light source 83. For some dental applications, it is desirable to have a substantially collimated beam directed towards the patient's oral cavity. In that case, lenses 87 and 88 can be selected so as to produce a collimated beam at the illumination plane. A person skilled in the art will understand that more or fewer lenses than lens 87 and lens 88 can be selected to achieve this desired result.

Referring to FIG. 4B, an optional diffuser 90 is shown in between lens 87 and lens 88. The diffuser 90 is configured to mix light within a light beam received from lens 87 in order to increase color uniformity of the light beam. For example, the mixing can be such that a homogenized beam is produced at the illumination plane. That is, the color of the light is substantially uniformly throughout the light beam at the illumination plane. Typically, the light emitted by an LED light source has a non-uniform spatial and angular distribution of color. For example, the spectral power distribution (and hence color) of the light beam can vary across the angular distribution of the LED and laterally across the emitting surface of the LED chip. Such color non-uniformity can result in a beam pattern at the illumination plane with objectionable color non-uniformity, such as bands of color. A diffuser can be used to reduce this undesirable effect by mixing the spatially distributed colors into a more homogeneous light beam, such as by scattering light to a limited extent.

However, if the diffusion is unlimited, or to a large degree, the beam pattern at the illumination plane may become unacceptably large. Thus, the degree of diffusion can be selected to balance the degree of mixing with the overall size of the beam pattern. As used herein, this balancing is referred to as controlled diffusion. That is, controlled diffusion is diffusion that is limited or that produces an incremental increase in the divergence of a light beam. It can also be referred to as angularly limited diffusion, weak refraction or weak diffraction. In general, a diffuser can be characterized by the divergence angle that it imposes on a received beam. Preferably, a controlled diffuser induces a small divergence angle on a substantially collimated light beam. Typically, a controlled diffuser is a diffuser that induces a divergence angle that is less than 10 degrees.

Referring to FIG. 4B, the diffuser 90 can be any device capable of producing controlled diffusion, such as, but not limited to, a light diffusing film or sheet separate from or attached to lens 88, an engineered diffuser, a pillow lens, an array of diverging microlenses, or a transparent optical element having a microstructured surface. For example, optical elements having a microstructured surface are available from commercial suppliers such as Luminit, RPC Photonics, and Fusion Optix. Desirably, the diffuser 90 has a high transmission efficiency and is substantially achromatic. In a particular implementation, the diffuser 90 is a transparent optical element having a microstructured surface, where the surface comprises random, non-periodic three dimensional holographic relief structures. In another implementation, the diffuser 90 is a transparent optical element having a periodic microstructured surface.

As shown in FIG. 4B, the diffuser 90 can be attached to or integrated into the lens 88. However, the diffuser 90 can be a separate element between lens 87 and lens 88. The diffuser 90 can also be located before lens 87, or at other locations within optics 82. In some implementations, the diffuser imposes between about 0.5 and about 5 degrees divergence on incident light. In other implementations, the diffuser imposes approximately a 2 degree divergence.

Typically, the diffuser 90 is included in a normal-mode illuminator. A cure-safe illuminator typically does not include a diffuser 90 when the color non-uniformity issues described above are not significant.

As an alternative to or in addition to the diffuser 90, other light-mixing devices can be used in the optics 82. Such light-mixing devices include, but are not limited to, a light pipe, a total internal reflection (TIR) collimator, TIR optical fiber, microlens array, other lenslet array, or combination thereof. Such light-mixing devices can be incorporated into the optics 82 and function to mix light within the light beam received from lens 87 in order to increase color uniformity of the light beam. Depending on the type of light-mixing device selected, one or more of the lenses 87 and 88 may not be needed to produce the desired illumination at the illumination plane. For example, if the light-mixing device is a TIR collimator, then the lens 87 may not be needed. Alternatively, if the light-mixing device is a TIR collimator, then neither lens 87 nor lens 88 may be needed.

Referring to FIG. 4B, light transmitted through the lens 88 is received by shaping lens 89. The shaping lens 89 provides a final shaping of the light beam emitted from the LED light source 83. In general, the shaping lens 89 modifies the beam so that it has a desired shape at the illumination plane. For example, it is typically desirable that the light at the illumination plane have an oval or rectangular shape in order to reduce patient eye glare. The shaping lens 89 can be integrated into or attached to the shield of the LED dental light. However, the shaping lens 89 can be a separate element from the optics 82 and from the shield. Although shown in FIG. 4B as a separate element from optics 82, the shaping lens 89 can be a part of the optics 82 and situated within the lens module 80. Further, the shaping lens functionality can be integrated into other lenses in the optics 82, such as lens 88 or 87, making an additional shaping lens 89 unnecessary. In some embodiments, the shaping lens 89 is an array of cylindrical lenses.

Figure 5A:
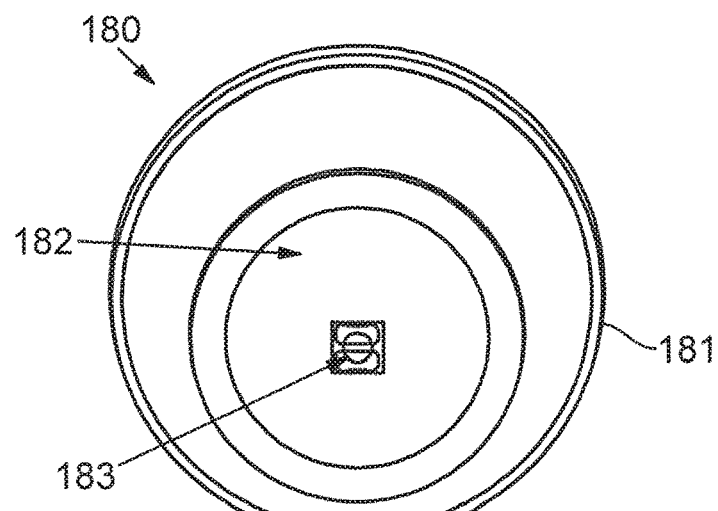
FIG. 5A is an elevation view of an exemplary lens module and LED light source.
Figure 5B:
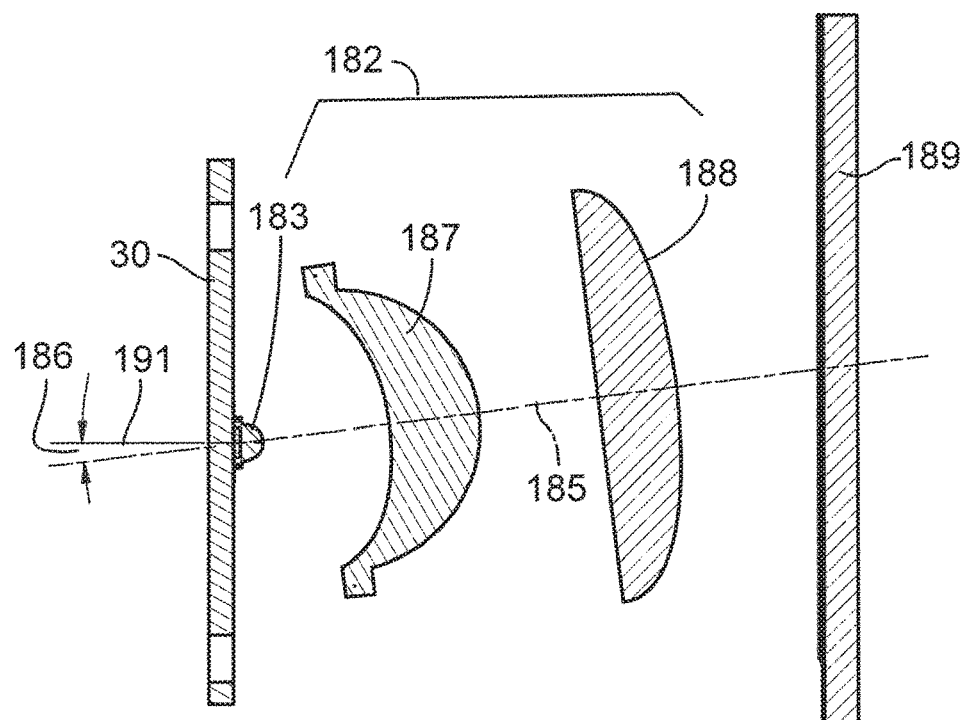
FIG. 5B is a cross-sectional view of a shaping lens and the lens module and LED light source of FIG. 5A.

FIG. 5A is an elevation view of another exemplary lens module and LED light source. As shown, a lens module 180 includes a lens housing 181 and optics 182. For clarity, the optics 182 are not shown in FIG. 5A. FIG. 5B is a cross-sectional view of FIG. 5A, and illustrates exemplary optics 182. The lens curvatures and spacing between optical elements shown in FIG. 5B are schematic and not drawn for scale. For purposes of illustration, the lens housing 181 is not shown in FIG. 5B. An LED light source 183, mounted to the substrate 30, is configured to produce a light beam that is received by optics 182. The optics 182 represent an exemplary collimating lens system, and comprise a lens 187 and a lens 188. Lenses 187 and 188 can be selected from lenses described herein, or others known in the art. In general, lens 187 and lens 188 can be selected to produce a desired beam pattern at the illumination plane. Light emitted from optics 182 is then transmitted through a shaping lens 189, which can be any shaping lens described herein.

Referring to FIG. 5B, an axis 185 defines an optical axis of the optics 182 and intersects the optics 182 at an approximate center. The axis 185 can be referred to as an illumination axis when it is parallel to and directed along the direction of propagation of light emitted from the optics 182 or the lens module 180. In the illustrated implementation, the axis 185 is shown to be displaced from an axis 191 by an angular displacement 186. The axis 191 is a normal axis that is perpendicular to the substrate 30 at an approximate center of the LED light source 183. Preferably, the axis 185 intersects axis 191 at the approximate center of the LED light source 183.

The optics 182 and the LED light source 183 can form an exemplary cure-safe illuminator. When used in this manner, the optics 182 can be selected so as to produce a cure-safe beam. As described above, a filter can be incorporated into the cure-safe illuminator to produce the cure-safe beam. For example, lens 188 can be dyed or tinted such that transmission of wavelengths of light below about 500 nm is substantially reduced. Alternatively, a film that is dyed or tinted could be attached to lens 188. In another example, lens 187 can be so modified. However, tinting of lens 188 may be preferred over tinting of lens 187 when the lens 188 is of more uniform thickness than lens 187. Uniform lens thickness allows for more consistent attenuation of blue light while reducing excessive attenuation of other wavelengths. In some examples, the filtering can be performed by an element separate from lenses 187 and 188.

In an example embodiment of a dual-mode LED dental light, the illuminators 6e-6l shown in FIG. 1 can be normal-mode illuminators and the illuminators 6a-6d can be cure-safe illuminators. Each of the normal-mode illuminators 6e-6l can include an LED light source and optics as illustrated in FIG. 4B. Furthermore, the angular displacement 86 of the normal-mode illuminators can be between about 4 and 5 degrees so that the illuminators 6e-6l produce light beams that substantially overlap at the illumination plane of the LED dental light 10. Each of the cure-safe illuminators 6a-6d can include an LED light source and optics as illustrated in FIG. 5B. Furthermore, the angular displacement 186 of the cure-safe illuminators can be between about 6 and 8 degrees so that the illuminators 6a-6d produce light beams that substantially overlap at the illumination plane.

As stated above, quality of light is also an important consideration when designing an LED dental light, and, specifically, when designing the illuminators to be used in an LED dental light. For example, it is common in the dental setting for dentists to prefer natural light when performing certain procedures. Natural light can assist in accurate diagnosis of soft and hard tissue disease and in performing shade-matching. Shade-matching is common during restoration procedures. For example, a patient may seek to have artificial teeth placed in her mouth or to have other dental restoration performed. It is important for the dentist to be able to match the color of the artificial teeth or restoration material to the color of the patient's original teeth in order to produce the most aesthetically pleasing result. Preferably, the shade of the original teeth matches that of the artificial teeth or restoration material. Natural light is the preferred light for determining such a match. However, natural light is not always available in a dental setting because the matching may be performed at night or inside of a building where windows allowing in natural light are not available. Thus, it is desirable for a dental light to mimic natural light as much as possible if shade-matching applications are to be performed using the dental light and to facilitate more accurate diagnosis of tissue disease. The closer a dental light is to mimicking natural light, the higher the quality of light.

Quality of light can be measured in at least three different ways. First, a color rendering index (CRI) can be used. Generally, the higher the CRI, up to 100, the higher the quality of light. LED dental lights described herein can have a CRI greater than 85. In some embodiments, the CRI is greater than 88, while in other embodiments the CRI is between 87 and 90. However, CRI is not always predictive of quality of light, or of color rendering performance, of an LED. Thus, other parameters are often considered when describing the quality of light emitted from an LED. Quality of light can also be measured by determining the correlated color temperature (CCT). CCT is a method for describing light color relative to the heating of an ideal black radiator. Pure white light has a CCT of about 5000 Kelvin (K). Dental practitioners commonly prefer the CCT value of a dental light to be as close as possible to about 5000 K. LED dental lights described herein can have a CCT of approximately 5000 K. However, the CCT of LED dental lights described herein can be between about 3500 K and about 6500 K.

Figure 10:
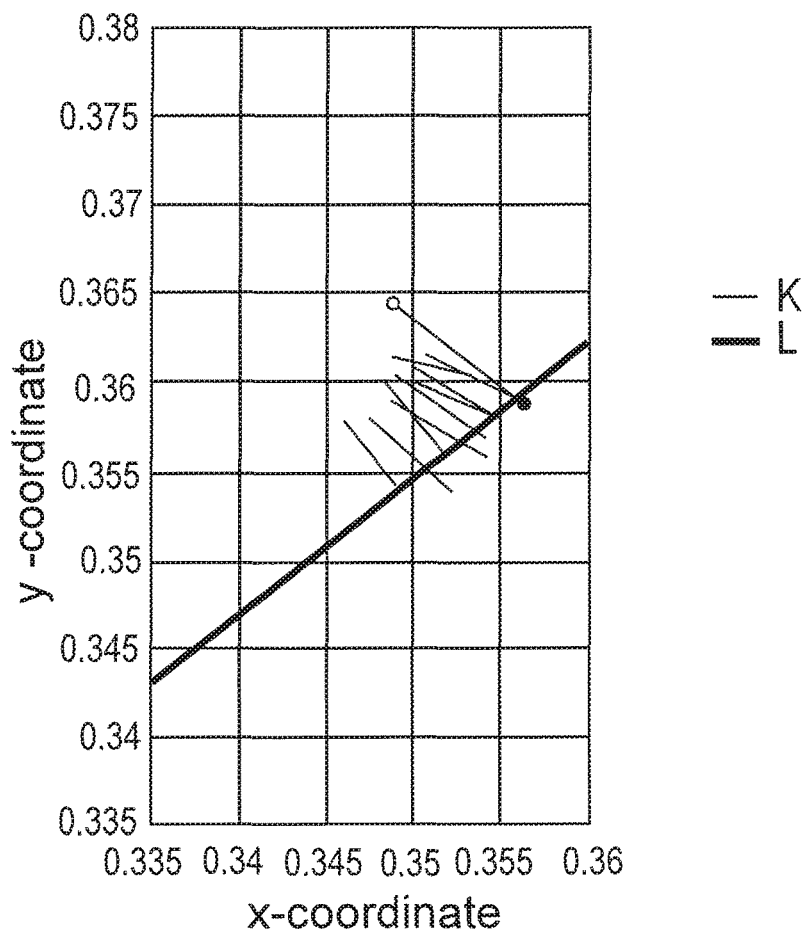
FIG. 10 is a plot of chromaticity coordinates for exemplary LED dental lights described herein.

Quality of light can also be measured by looking to International Commission on Illumination (CIE) chromaticity coordinates. Several CIE standards exist for determining preferred chromaticity coordinates. The Planckian black body locus represents one possible standard, and it is the standard selected to be used in this application. However, a person of ordinary skill in the art would understand that a different CIE Standard Illuminant, such as D50, D55 or others, could similarly be used to assess quality of light as discussed herein. In general, light is closer to mimicking natural light when the CIE chromaticity coordinates lie closer to the Planckian black body locus. In FIG. 10, the CIE x and y chromaticity coordinates of the Planckian black body locus are represented by a line L. LED dental lights described herein are represented by lines K. As shown in the figure, the chromaticity coordinates K of the LED dental lights move towards the Planckian black body locus L, demonstrating high quality of light. For example, the open dot represents the CIE chromaticity coordinates (i.e., CIE (x, y)) for a particular LED light source (e.g., as measured using an integrating sphere or nearly perfect reflective surface). As shown in the figure, the LED light source is more than 0.005 units off of the Planckian locus, as measured along the length of the line K. The closed dot represents the CIE chromaticity coordinates for the particular LED light source when incorporated into an LED dental light described herein and as measured at the illumination plane. As shown, the closed dot is approximately on the Planckian locus, or line L. Thus, the particular LED light source experiences a shift in chromaticity coordinates towards the Planckian locus of greater than 0.005 units when it is incorporated into the LED dental light. As shown in FIG. 10, other LED light sources represented by lines K experience shifts in chromaticity coordinates of at least 0.002 units, while other sources experience shifts of at least 0.004 units.

Although it is preferred that the LED dental light produce high quality of light, high quality of light may not be required when the LED dental light is operating in a cure-safe mode. For example, dentists typically perform shade-matching and tissue diagnosis when the LED dental light is operating in a normal mode. If this is the case, cure-safe illuminators may not need to exhibit a CCT close to 5000 K, chromaticity coordinates close to the Planckian black body locus, or a high CRI.

The quality of light emitted by an illuminator used in an LED dental light depends on various different factors. For example, the quality of light can depend on the quality of light of the particular LED light source used in the illuminator. Also, the quality can depend on the optics selected to be used in the illuminator and how these optics are arranged. Typically, an LED light source with high CRI is preferred. However, optics can be selected so as to improve the CRI of the LED light source. Further, an LED light source with chromaticity coordinates close to the Planckian black body locus is typically preferred. However, optics can be selected so as to shift the chromaticity coordinates of the LED light source towards the Planckian black body locus.

Figure 8:
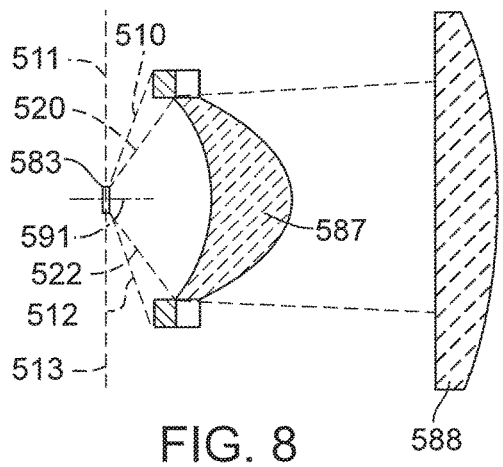
FIG. 8 is a cross-sectional view of an exemplary lens system for increasing a color rendering index (CRI) of an LED light source.

For example, FIG. 8 is a cross-sectional view of an exemplary lens system for increasing the quality of light emitted by an LED light source. In FIG. 8, lines 510, 511, 512, 513, 520, 522 represent rays of light propagating from the LED light source 583. In the illustrated two-dimensional view, the area between lines 511 and 513 represents an angular distribution of the light beam emitted from the LED light source 583, and the angles of propagation of the light in the light beam can be measured from the normal 591, which is perpendicular to the LED light source 583 at an approximate center. As shown in the figure, the light rays 520 and 522 are accepted by the lens 587 and consequently received by the lens 588, while the light rays 510 and 512 are rejected by the lens 587. The effective collection angle of the lens 587 is the angle defined by rays 520 and 522. In this manner, the angular distribution of the light beam emitted from the LED light source 583 is reduced. This reduction in the angular distribution of the light beam emitted from the LED light source improves the quality of light emitted by the LED light source 583 by increasing the CRI of the LED and by shifting the chromaticity coordinates of the LED towards the Planckian black body locus, as described above with reference to FIG. 10. As discussed above, the approach illustrated in FIG. 8 for improving quality of light is extendable to other CIE standards for determining preferred chromaticity coordinates.

Additionally, the lens system illustrated in FIG. 8 can include an aperture so as to further reduce the angular distribution of the light beam emitted from the LED light source 583. In this manner, the aperture would also function to improve the quality of light emitted by the LED light source 583.

The quality of light emitted by the LED light source 583 is improved because the LED light source 583 produces light having a non-uniform distribution of color. That is, the spectral power distribution (and hence color) of the light within the light beam emitted from the LED light source 583 varies as a function of angle as measured from the normal 591. Typically, the light emitted by an LED light source has a non-uniform spatial and angular distribution of color. For example, the spectral power distribution of the light beam can vary across the angular distribution of the LED and laterally across the emitting surface of the LED chip. Although the spectral power distribution of the light within the light beam varies across both a spatial and angular distribution, this variation in color may be referred to herein simply as a variation in color across the angular distribution of the light beam because the angular variation often dominates.

Because the light beam emitted by the LED light source 583 exhibits such color non-uniformity, reducing the angular distribution of the light beam, as shown in FIG. 8, can increase the CRI of the LED and shift the chromaticity coordinates of the LED in a favorable manner. In some embodiments, the CRI of the LED light source 583 is increased by at least about two units, while in other embodiments, the CRI is increased by between two and four units. Reducing the angular distribution of the light beam emitted from the LED light source 583 functions to improve the CRI when the portion of the light beam that lies closer to the normal has a higher CRI than the overall CRI of the LED light source 583. By collecting only a central portion of the angular distribution and rejecting the remainder, a higher CRI is achieved. The area of lens 587 functions in the illustrated implementation to define an effective collection angle and thereby increase the CRI of the LED light source 583. In some embodiments, the effective collection angle is less than about 60 degrees, while in other embodiments the effective collection angle is approximately 53 degrees.

The configuration shown in FIG. 8 for improving quality of light is counter intuitive. Typically, an optical system is designed in order to achieve the highest possible efficiency and illuminance. That is, the optical system is designed so as to maximize its angle of acceptance, or the collection angle of the optical elements within the system, in order to maximize the light received by and transmitted through the optical system. A reduced collection angle, as shown in FIG. 8, would ordinarily be viewed by an optics engineer as an inefficiency or a design flaw. Thus, the configuration shown in FIG. 8 would normally be avoided. Surprisingly, however, reducing the efficiency and illuminance of an optical system in the described manner can improve the quality of light emitted by LED dental lights described herein.

Referring back to FIGS. 4, 5, and 7, a shaping lens can be used to perform a final shaping of the light beams produced by the LED light sources. In some embodiments described herein, such as the LED dental light 10 of FIG. 1, this shaping function is performed by the front shield 4. FIG. 11A illustrates an example of such a shield. In the figure, an exemplary LED dental light shield 704 is shown with integrated shaping lenses 720. The shield 704 is made from a transparent material and can be flat to facilitate cleaning. The shield 704 functions to shape light emitted from illuminators positioned behind the shield. In general, the shield 704 refracts the transmitted light along a refraction axis 710. Correspondingly, this refraction causes the beam pattern produced at the illumination plane by the transmitted light to be elongated within the illumination plane in a direction parallel to the refraction axis 710.

FIG. 11B is a cross-sectional view taken along the line 11B-11B in FIG. 11A. Referring to FIG. 11C, a cross-sectional view taken along the line 11C-11C in FIG. 11A provides an enlarged view of the shaping lenses 720. As shown, the shaping lenses 720 are integrated into an inner surface 726 of the shield 704. Illuminators as described herein can be incident on the inner surface 726 so as to transmit light through the shield 704. Also shown is an integrated snap feature 712 which can facilitate attachment of the shield 704 to front housing 714.

FIG. 11D is an enlarged view of the region 11D in FIG. 11C illustrating shaping lens 720 having a width 724 and a height 722. As shown, the lens 720 is convex in shape, with respect to illuminators incident on the inner surface 726. Because the lenses 720 extend along the inner surface of the shield in a direction perpendicular to the refraction axis 710, the lenses 720 can be referred to as an array of cylindrical lenses. When used with illuminators, the width of the shaping lens 720 is typically such that each illuminator transmits light through more than one shaping lens 720. That is, the width of the shaping lens 720 is typically less than the width of an illuminator.

Although shaping lenses such as shaping lenses 720 are optional in an LED dental light, such lenses can facilitate accurate positioning or repositioning of the LED dental light in the direction of the refraction, and therefore improve the experience of a dental patient. Furthermore, because a patient's head may move during the dental procedure, it can be desirable for the LED dental light to have an oval or rectangular-shaped beam pattern at the illumination plane. The shaping lenses 720 can be configured to refract light so as to assist in formation of such an oval-shaped pattern.

Another important consideration when designing an LED dental light is providing a mechanism for dissipation of heat produced by the LED light sources. Referring to FIGS. 12-14, in some implementations, LED dental lights described herein are configured to facilitate heat transfer between the LED light sources and the dental light housing. FIGS. 12-14 illustrate views of a specific implementation of the LED dental light of FIG. 1. FIG. 13 is a cross-sectional view of the LED dental light 800 illustrated in FIG. 12. In FIG. 13, a shield 858 is shown connected to a front housing 854, which is attached to a rear housing 850. A gasket 857 creates a seal where the shield 858 connects to the front housing 854. A central area at 852 of the rear housing 850 can be mounted to a pivot assembly to facilitate positioning of the LED dental light 800.

FIG. 14 is an enlarged view of the region 14 in FIG. 13. As shown, a lens module 840 containing a lens 887 is mounted to an optical base 834, which is then mounted to a substrate 830. Also shown is an aperture 884 as part of the optical base 834. The rear housing 850 is shown attached directly to the substrate 830 at a pillar or web 871. Optionally, the pillar 871 is integrally formed with the rear housing 850. The area of attachment between the rear housing 850 and the substrate 830 is at the location of the LED light source 883. This type of attachment can be desirable to facilitate heat transfer between the LED light source 883 and the rear housing 850. For example, LED light sources generate heat when activated. However, if the heat is not dissipated sufficiently, the localized temperature rises and the life expectancy of the LED light source can be reduced. The spectral power distribution of the LED light source can also be adversely affected by a temperature rise, which can compromise quality of light produced by the dental light. Thus, a mechanism for dissipating heat is preferable. When an LED dental light is designed in accordance with FIGS. 13-14, desirable heat dissipation can be achieved in some embodiments without the need for active cooling or air vents. A lack of air vents can enable the LED dental light 800 to be a fully enclosed optical system and circuit board, if desired. Such a fully enclosed system can reduce contamination and damage to the optical and electrical components from dust, fluids, or cleaning chemicals.

The pillar 871 can facilitate heat transfer from the LED light source 883 to the rear housing 850. In some embodiments, a thermally conductive, electrically insulating material (such as a pad, gel, paste, etc.) is situated between the rear housing 850 and the substrate 830 at the area of attachment to further facilitate heat transfer. Although heat transfer can be facilitated without the use of a pillar 871, the pillar 871 allows there to be space between the substrate 830 and the rear housing 850 to fit electronics that may be attached to the substrate 830.

In order to further facilitate heat transfer between the LED light source 883 and the rear housing 850, the substrate can be a thermally conductive printed circuit board, such as any metal clad circuit board known in the art. For example, the printed circuit board can have a substrate (or thermally conductive substrate layer), a dielectric layer, and a circuit layer. The thermally conductive substrate layer can comprise aluminum, copper or other thermal conductor. Heat transfer may be improved when the circuit board has a thicker thermally conductive substrate layer, a thinner dielectric layer, and copper pours connected to the LED light sources. In some embodiments, the thermally conductive printed circuit board has a total thickness of about 0.056" or greater, the dielectric layer has a thickness of about 0.003" (76 microns) or less, the circuit layer has a thickness of about 2 ounces/square feet or greater, and the copper pours extend from each LED pad with a minimum area of about 0.07 square inches. The dielectric material can have a thermal impedance of about 0.065° C./W and a conductivity of about 1.3 W/m-K or greater. However, the dielectric material can have a thickness of between about 0.0015" (38 microns) and about 0.009" (229 microns), a thermal impedance of between about 0.3° C./W and about 1.1° C./W, and a conductivity of between about 1.1 W/m-K and about 3.0 W/m-K. Further, the circuit layer can have a thickness of between about 1 ounce/square feet and about 3 ounces/square feet.

To further facilitate heat transfer, the rear housing 850 can be made of a metal or other thermally conductive material. In addition, the LED light source 883 can be positioned with respect to other LED light sources mounted to the substrate 830 so as to reduce localized temperature rise. For example, the LED light sources can be positioned with respect to one another so that the effect from heat produced by neighboring LED light sources is minimized. In one example, the LED light sources are spatially separated on the substrate by a distance of about 1.4" or greater. Alternatively, the LED light sources can be spatially separated on the substrate such that there is at least about 1" spacing per 1 Watt of power per LED light source. Further, the LED light sources can be coupled to a single substrate or to multiple substrates.

LED dental lights as described herein are typically mounted to additional mechanisms to facilitate positioning by a user. FIGS. 15-18 illustrate exemplary mechanisms for positioning an LED dental light. Referring to FIG. 15, a rear portion of an LED dental light 900 is illustrated attached to an exemplary pivot assembly 948. The LED dental light 900 has a rear housing 950 and handles 8. The pivot assembly 948 can be attached to the rear housing 950 at a central portion 952 that is recessed into the rear housing 950. The pivot assembly 948 can be attached to the rear housing with exposed screws 944 to allow the LED dental light 900 to be removed from the pivot assembly 948 to facilitate replacement and servicing. The pivot assembly 948 can also be attached to the rear housing 950 with a joint friction adjustment screw 947. The screw 947 can use spring tension to clamp a bearing piece into the pivot axles in order to allow the level of friction in the joint to be adjusted both in the factory and by the end user. The pivot assembly 948 includes a pivot arm 946 that is capable of rotational motion into the recess 951 in the rear housing 950. The recess 951 allows the pivot assembly to operate. Also, the recess 951 can allow the pivot assembly to be attached to the rear housing 950 at the center of mass of the LED dental light 900. Such a connection can reduce joint friction and make the joint much easier to operate.

An exploded perspective view of the component parts of the pivot assembly 948 is shown in FIG. 16. The pivot assembly 948 includes a pivot arm 946 with a forked bracket 941. The pivot arm 946 can be hollow so as to allow wires to run through the fork at a wiring passage 945. In this manner, movement and bending of the wires can be reduced, which reduces risk of wiring failure.

Figure 17:
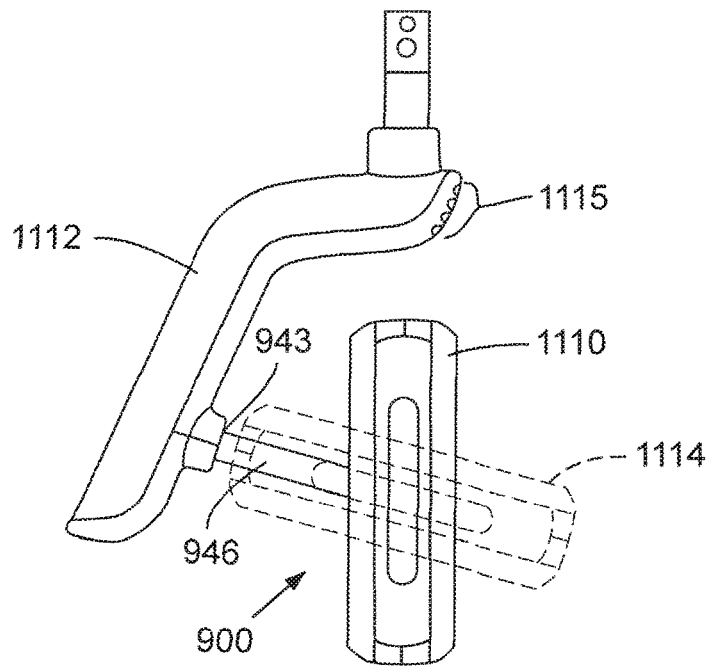
FIG. 17 is a side elevation view showing a range of rotational motion of the LED dental light.

The rotational motion of the pivot assembly 948 is illustrated in FIG. 17, which provides a side view of the LED dental light 900 and arm 1112. At position 1114, the LED dental light 900 is at a lower rotational limit, and the pivot arm 946 is fitted within the recess 951. At position 1110, the LED dental light 900 is at an upper rotational limit. In some embodiments, the total operating range, defined as the range of motion between the upper and lower rotational limit, is at least 105 degrees.

Figure 18:
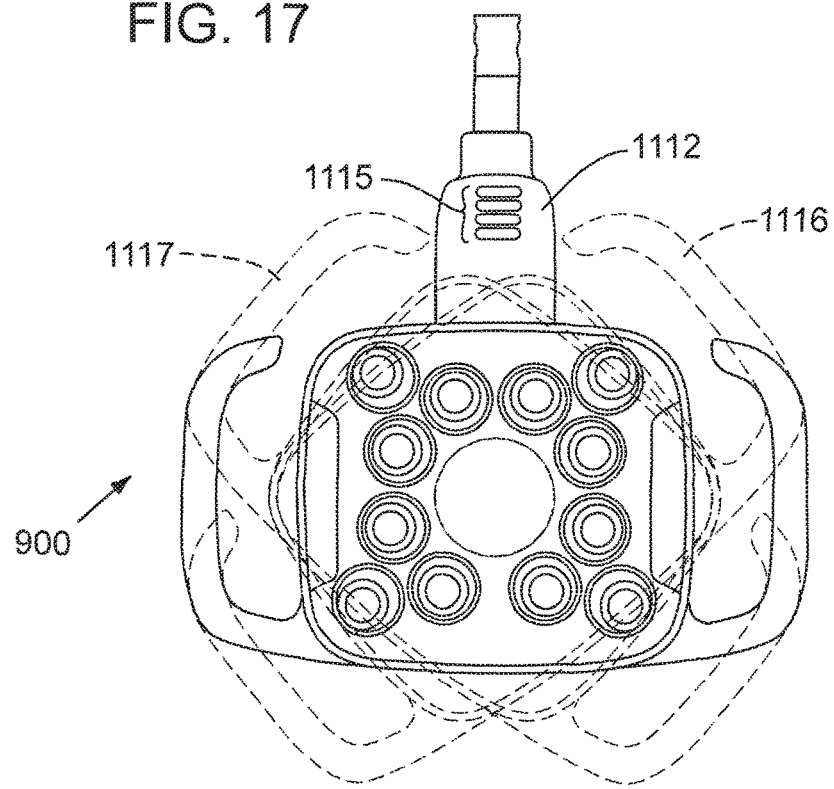
FIG. 18 is a front elevation view showing a range of rotational motion of the LED dental light.

Referring to FIG. 17, the LED dental light 900 can be attached by the pivot assembly 948 to the arm 1112. For example, as shown in FIG. 16, a pivot housing 943 can be connected to the pivot arm 946 by a plastic sleeve bearing 942, a rotation stop 937, and a joint friction adjustment screw 938. The pivot housing 943 can then be connected to an arm 1112. The rotational motion of this attachment is shown in FIG. 18, which provides a front view of the LED dental light 900 and the arm 1112. At position 1116, the LED dental light 900 is in a first rotational position. At position 1117, the LED dental light 900 is in a second rotational position. A total operating range, defined as the range of motion between the first and the second rotational positions, can be at least 80 degrees in some embodiments.

In some embodiments, the arm 1112 can have indicators 1115, as illustrated in FIGS. 17 and 18. The indicators can be backlit illuminated regions or other illuminated displays, and, although a series of indicators 1115 are shown in the figures, more or fewer indicators can be provided. The indicators 1115 can indicate the current operating setting of the LED dental light, or other light functionality. Exemplary operating settings include, but are not limited to, intensity settings, normal-mode operation, or cure-safe operation. For example, the indicators can indicate to an operator viewing the indicators what intensity (e.g., illuminance) setting, or other functional setting, is currently selected. Additionally, the indicators can indicate how many times a selector switch must be actuated to select the cure-safe mode. In one implementation with a series of four indicators, illumination of one of the indicators can indicate care-safe operation, while illumination of the other three indicators (individually or in combination) can indicate which of three illuminance settings are activated during normal mode operation. In one implementation with a single indicator, the single indicator can change in appearance based on the current operating setting. For example, the indicator can change in color, display different numbers, or display different pictures or graphics based on the current operating setting.

Although the indicators 1115 are shown in a particular location on arm 1112, the indicators can be placed in a different location. However, it is preferable that the indicators be positioned so that viewing by an operator is convenient and not difficult. For example, it is preferable that an operator be able to quickly recognize the setting of the dental light from various different viewing angles. Indicators 1115 located on or near to the dental light 900 are generally convenient for viewing by an operator. But, indicators 1115 located directly on or adjacent to the front face of the LED dental light 900 may be obstructed from the operator's view in some circumstances. For example, because the dental light 900 is mounted to a pivot arm 946 and capable of pivoting about one or more axes, the orientation of indicators located on the dental light can vary, thereby making it more difficult for an operator to quickly locate and interpret the information provided by the indicators. Furthermore, an operator may have difficulty seeing the front face of the dental light 900 during some dental procedures, particularly if the operator is seated to the side or at an elevated position relative to the dental light 900. Thus, it may not be desirable to locate the indicators 1115 directly on or adjacent to the front face of the LED dental light 900.

For more convenient viewing, it is generally desirable to position the indicators 1115 such that the orientation of the indicators is minimally obstructed by the position of the dental light 900 and such that the indicators 1115 are viewable from a wide range of viewing angles relative to the front view of the arm 1112 (as shown in FIG. 18). For example, referring to FIGS. 17 and 18, the indicators 1115 maintain vertical orientation (i.e., the indicators may move up and down, but will not rotate side to side or tilt forward or back) despite repositioning of the dental light 900 because the arm 1112, as shown, pivots about one axis only—the vertical axis. Further, regardless of the rotational motion of the LED dental light 900, the indicators 1115 remain substantially unobstructed from the front and side views shown in FIGS. 17 and 18. In addition, the forward facing surface of the arm 1112 (shown in FIG. 18) can be curved, and the indicators 1115 to extend laterally along this curved surface. In this manner, the indicators 1115 can be viewable from a wide range of viewing angles. For example, as shown in FIG. 17, such a curved surface facilitates viewing of the indicators 1115 from the side, which is a viewing angle of 90 degrees relative to the front view of the arm 1112. Such a curved surface can also facilitate viewing from viewing angles of more than 90 degrees relative to the front view of the arm 1112.

LED dental lights as described herein are typically implemented with various electronics for controlling functions of the light. Such electronics can be included within the housing of the LED dental light, or as part of the separate housing. In an exemplary implementation of a dual-mode LED dental light, the LED light sources of the dental light can be controlled by an LED driver capable of supporting dual-mode operation. The LED driver can be a single or multichannel LED current regulator configured to provide multichannel output and buck-boost current regulation (i.e., a so-called buck-boost regulator). The buck-boost regulator can be selected from those known in the art. In some embodiments, the buck-boost regulator is a Single-Ended Primary Inductance Converter (SEPIC). A buck-boost regulator can provide an output voltage necessary for a specific load regardless of the relationship between the input voltage and the output voltage. This allows the driver to drive two different loads, and thereby support both normal and cure-safe modes of operation. For example, a buck-boost current regulator allows an input voltage to be greater, equal, or less than the output voltage.

Such a current regulator can maintain color consistency of the LED light sources by maintaining consistent current to each LED. The LED light sources can be arranged in series and connected to the current regulator. When connected in series, LED protection devices can be included to allow for current to flow through each LED regardless of an LED failure. Pulse-width modulation (PWM) dimming can allow for consistent color and CRI when dimming. Analog dimming can be used to reduce the intensity, however, analog dimming is nonlinear and can skew CCT and CRI. As consistent color and CRI are desired for all modes of operation, PWM dimming is usually preferred.

The LED driver can dynamically regulate current through two strings of LED light sources. For example, the first string can connect LED light sources dedicated to normal-mode operation. This mode can also be called a white light mode. The second string can connect LED light sources dedicated to a cure-safe operation. A user of the LED dental light can control whether the LED dental light operates in cure-safe or normal mode. Typically, the LED light sources will be connected in series. Because the LED lights are dedicated to a particular mode, the LED light sources in the first string will not typically be activated at the same time as the LED light sources in the second string, and vice versa. The strings can operate independently of each other. That is, the strings can be arranged in parallel with respect to each other. The first string can be connected to a first output of the LED driver and the second string can be connected to a second output of the LED driver.

As discussed above, the LED driver can be capable of dimming. For example, the LED driver can be configured to provide a plurality of PWM levels of dimming when a string is activated. For example, when the LED dental light is in normal-mode operation, the LED driver can produce three levels of intensity output. The level of intensity output can be selected by the user. In one implementation, a high illuminance setting produces light having an intensity of between about 25,000 lux and 35,000 lux, a medium illuminance setting produces light having an intensity of between about 18,000 lux and 30,000 lux, and a low illuminance setting produces light having an intensity of between about 10,000 lux and 20,000 lux. Further, cure-safe operation produces light having an intensity of between about 18,000 lux and 30,000 lux. In another implementation, a high illuminance setting produces light having an intensity of about 30,000 lux, a medium illuminance setting produces light having an intensity of about 25,000 lux, and a low illuminance setting produces light having an intensity of about 15,000 lux. Further, cure-safe operation produces light having an intensity of about 25,000 lux.

Figure 21:
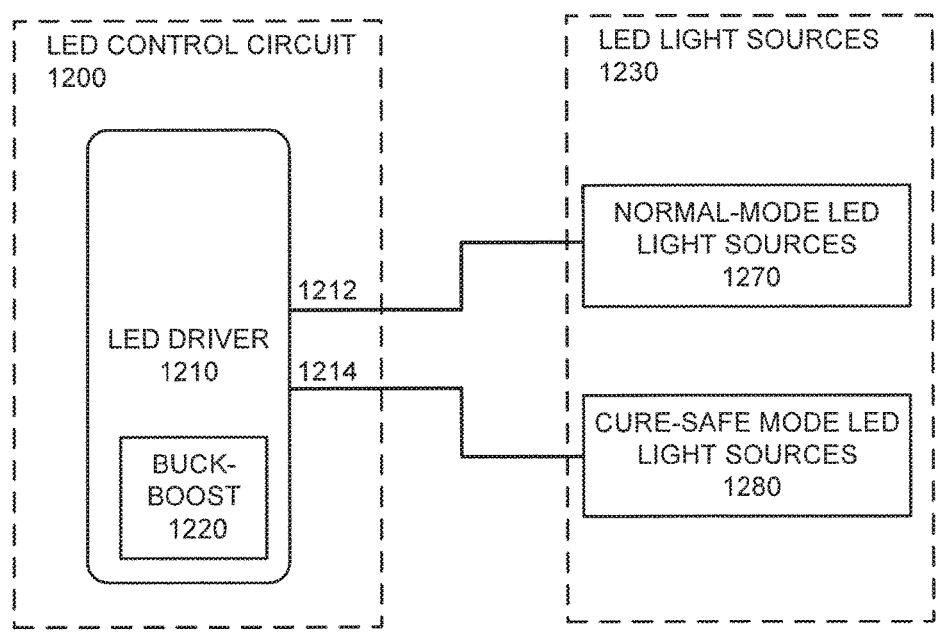
FIG. 21 is a schematic of an exemplary control circuit for an LED dental light.

Referring to FIG. 21, an exemplary LED driver 1210 is shown within an exemplary LED control circuit 1200. The LED driver 1210 can include a buck-boost current regulator 1220. The LED light sources 1230 are organized into two strings: normal-mode LED light sources 1270 and cure-safe LED light sources 1280. The LED driver 1210 has a first output 1212 that electrically couples the driver to the string of normal-mode LED light sources 1270. The LED driver 1210 also has a second output 1214 that electrically couples the driver to the string of cure-safe LED by sources 1280. Thus, the LED driver 1210 is configured to operate a dual-mode LED dental light.

Figure 22:
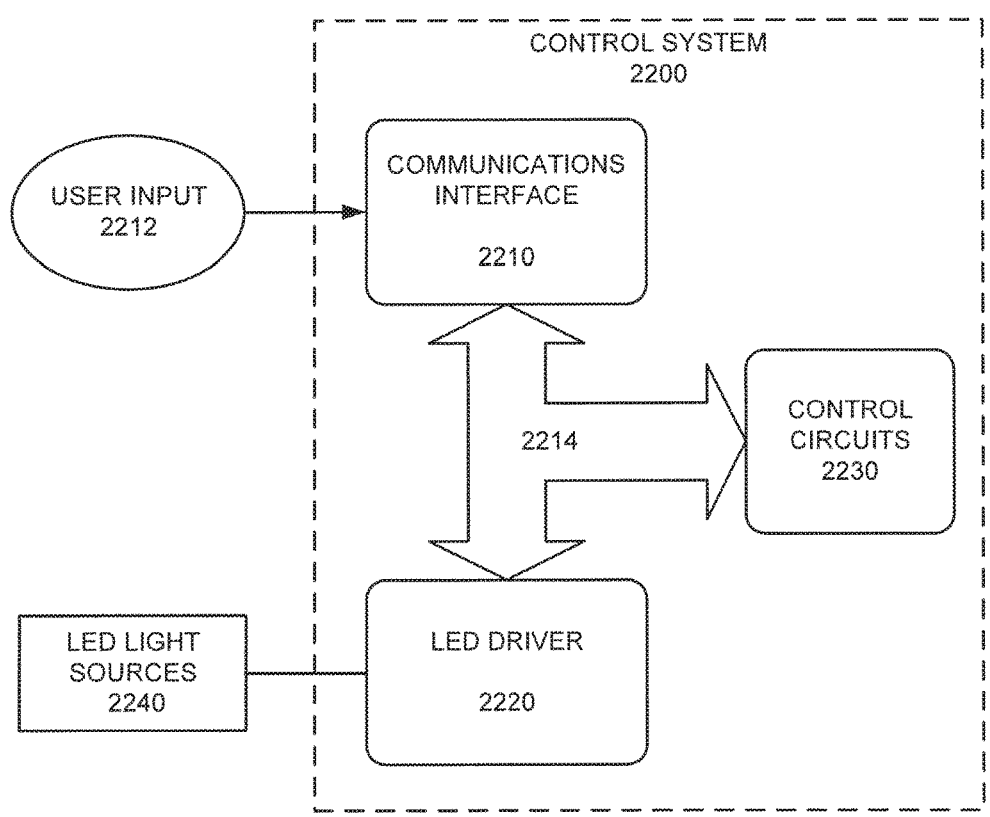
FIG. 22 is a schematic of an exemplary control system receiving user input.

In general, operation of the LED dental light can be controlled by a user. FIG. 22 illustrates an exemplary control system 2200 for an LED dental light. As shown, a user provides input 2212 to the dental light control system via a communications interface 2210. For example, the user may provide input to the control system via a mechanical switch, series of buttons, interactive display, mouse, keyboard, or other device known in the art for facilitating user control of a system. The user input 2212 may correspond to a request that the dental light be placed in cure-safe or in normal-mode operation, a request to turn the dental light on or off, a request to change intensity of the light, or to trigger other functionality of the dental light. The user input is then transmitted as a command or message via a controller-area network (CANbus) cable 2214.

The CANbus cable 2214 provides a means for communicating data, such as messages and commands, between control circuits 2230, the LED driver 2220, and the communication interface 2210. The CANbus cable 2214 can also function to transmit power to the LED light sources. For example, the CANbus cable 2214 can operate as a combo-cable, combining data communication and power.

The control circuits 2230 represent electronics connected to the LED dental light configured to perform other functionalities of the LED dental light. The LED driver 2220 is shown connected to the LED light sources 2240. The LED driver 2220 can receive data via the CANbus cable 2214 and control the LED sources 2240 in the appropriate manner. For example, if the LED driver 2220 receives a message via the CANbus cable 2214 to turn the LED dental light on, the LED driver 2220 can respond by activating LED light sources 2240.

In view of the many possible embodiments to which the principles of the disclosed invention may be applied, it should be recognized that the illustrated embodiments are only preferred examples and should not be taken as limiting in scope. Rather, the scope is defined by the following claims. We therefore claim all that comes within the scope and spirit of these claims.

We claim:

1. A light for use in a dental examination setting for illuminating an oral cavity of a patient, the light comprising:
    a housing unit for connecting the light to an arm assembly for positioning the light within the dental examination setting;
    a plurality of light emitting diode (LED) light sources coupled to the housing unit for producing respective light beams along a plurality of respective paths;
    a substrate coupled to the housing unit and defining a substrate plane, wherein the plurality of LED light sources are mounted to the substrate;
    a plurality of lens modules coupled to the substrate, wherein each of the plurality of lens modules is tilted relative to the substrate plane and positioned to receive a respective light beam from one of the plurality of LED light sources, further wherein the respective light beams transmitted by the modules combine to form a beam pattern in an illumination plane defined within an oral cavity of a patient;
    a plurality of collimating lenses mounted within the plurality of lens modules, wherein each of the plurality of lens modules is situated along one of the paths to receive the respective light beams from the plurality of LED light sources and to perform collimating action on the received light beams;
    a plurality of diffusers mounted within the plurality of lens modules, wherein each of the plurality of diffusers is situated along one of the paths to impose a divergence on the respective light beams from the plurality of collimating lenses; and
    a plurality of two-dimensional apertures having a short axis and a long axis and mounted within the plurality of lens modules, wherein each of the plurality of apertures is situated along one of the paths, upstream from one of the plurality of collimating lenses, for receiving the respective light beams from the plurality of LED light sources, further wherein the plurality of apertures transmit substantially two-dimensional shaped light beams that substantially overlap in the illumination plane.

2. The light of claim 1, further comprising:
    a series of substantially parallel cylindrical convex lenses, each having a length and a width, wherein the widths of the cylindrical convex lenses are parallel to the long axes of the plurality of apertures and the received light beams are spread in a direction that is parallel to the widths of the cylindrical convex lenses.

3. The light of claim 1, wherein the paths of the respective light beams produced by the LED sources are along normal axes that are perpendicular to the substrate plane at an approximate center of the LED light source and wherein the respective light beams transmitted by the modules define respective illumination axes that are displaced from the respective normal axes such that the light beams substantially overlap in the illumination plane.

4. The light of claim 1, wherein each aperture receives the respective light beams directly from the LED light source.

5. The light of claim 1, wherein the plurality of collimating lenses is a first plurality of collimating lenses, further comprising:
    a second plurality of collimating lenses mounted within the plurality of lens modules, each of the second plurality of collimating lenses being situated along one of the paths for receiving the respective light beams from the plurality of diffusers and for performing collimating action on the received light beams.

6. The light of claim 1, wherein the plurality of diffusers are transparent optical elements having microstructured surfaces.

7. The light of claim 2, wherein the widths of the cylindrical convex lenses are such that each light beam received from the plurality of diffusers is transmitted through more than one of the cylindrical convex lenses.

8. A light for use in a dental examination setting for illuminating an oral cavity of a patient, the light comprising:
    a housing unit for connecting the light to an arm assembly for positioning the light within the dental examination setting;
    at least two light emitting diode (LED) light sources coupled to the housing unit for producing respective light beams along at least two respective paths, wherein the light beams combine to generate a beam pattern in an illumination plane defined within an oral cavity of a patient;

a first collimating lens assembly, the first collimating lens assembly situated along one of the paths to receive the respective light beams from the at least two LED light sources and to perform collimating action on the received light beams;

at least two transparent optical elements each situated along one of the paths to receive the respective light beams from the first collimating lens assembly and having a microstructured surface to scatter light within the received light beams to a limited extent; and a second collimating lens assembly, the second collimating lens assembly being situated along one of the paths, downstream from the first collimating lens assembly, for receiving the respective light beams from the at least two diffusers and for performing collimating action on the received light beams.

9. The light of claim 8, wherein the microstructured surfaces of the at least two transparent optical elements are configured to scatter light within the received light beams to a limited extent that is not sufficient to cause complete spectral homogenization within the received light beams.

10. The light of claim 8, wherein the microstructured surfaces of the at least two transparent optical elements are configured to uniformly scatter the received light beams.

11. The light of claim 8, further comprising at least two apertures each situated along one of the paths, upstream from the first collimating lens assembly, for receiving the respective light beams from the at least two LED light sources and for transmitting substantially rectangular-shaped light beams that reduce a width of the beam pattern in the illumination plane in the direction of the patient's eyes.

12. The light of claim 8, wherein the microstructured surfaces of the at least two transparent optical elements are each configured impose a divergence on respective received light beams of between 0.5 and 5 degrees.

* * * * *